United States Patent [19]
Moberg et al.

[11] Patent Number: 5,951,595
[45] Date of Patent: Sep. 14, 1999

[54] SETSCREWLESS CONNECTOR ASSEMBLY FOR IMPLANTABLE MEDICAL DEVICES

[75] Inventors: Sheldon B. Moberg, Granada Hills; Buehl E. Truex, Glendora; Alfred D. Acken, deceased, late of Sylmar, by Ryan G. Rodriguez, executor; Clyde K. Nason, Valencia; William H. Stutz, Jr., Eagle Rock; Edward Gene Rourke, Topanga, all of Calif.

[73] Assignee: Pacesetter, Inc., Sylmar, Calif.

[21] Appl. No.: 08/852,161

[22] Filed: May 6, 1997

Related U.S. Application Data

[60] Provisional application No. 60/017,807, May 13, 1996.

[51] Int. Cl.$^6$ .............................. A61N 1/375; H01R 17/18
[52] U.S. Cl. ........................... 607/37; 439/909; 439/836; 439/838; 439/851
[58] Field of Search ....................... 607/36–38; 439/909, 439/851, 838, 836, 816, 669, 668, 370, 371, 271–275

[56] References Cited

U.S. PATENT DOCUMENTS

| | | |
|---|---|---|
| 4,278,093 | 7/1981 | Lafortune et al. . |
| 4,456,320 | 6/1984 | Gallusser et al. ..................... 339/94 M |
| 4,614,390 | 9/1986 | Baker ..................................... 339/61 R |
| 4,934,366 | 6/1990 | Treux et al. ............................... 607/36 |
| 5,766,042 | 6/1998 | Riies et al. ............................... 439/668 |
| 5,807,144 | 9/1998 | Sivard ..................................... 439/816 |

*Primary Examiner*—Jeffrey R. Jastrzab

[57] ABSTRACT

A connector assembly mounted on an implantable cardiac stimulation device has an actuator mechanism for fixing and sealing electrical leads inserted into lead receptacles within the connector assembly without the use of setscrews. Fixing and sealing of the leads is accomplished by compressing resilient lead lock seals of O-ring shape, disposed in annular recesses, with lip portions of a plunger drawn toward the molded support by the actuator mechanism. In a first embodiment of the actuator mechanism, rotation of a cam actuator transversely journaled within the support, using a torque wrench or similar tool, moves a cam slide attached to the plunger through a fixed displacement between lock and unlock positions as an offset camming portion of the actuator engages the surfaces of a slot within the cam slide. In a second embodiment, constant-force compression of the lead lock seals by the plunger is provided by using a torque wrench to rotate a screw actuator having one end coupled to the plunger and an opposite threaded end received within a screw block transversely disposed within the support. In a third embodiment, a rotatable toothed pinion engages a toothed slot within a slidable rack to provide incremental advancement of the rack, and thereby stepped displacement and force, with a resulting increased resolution. In a fourth embodiment, compliance provided by either a spring formed within the cam slide, or a spring nut mounted thereon, prevents excessive force from being exerted on leads of larger diameter.

50 Claims, 17 Drawing Sheets

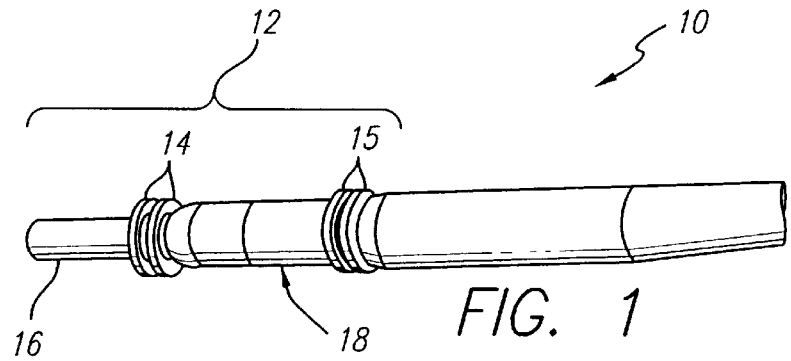
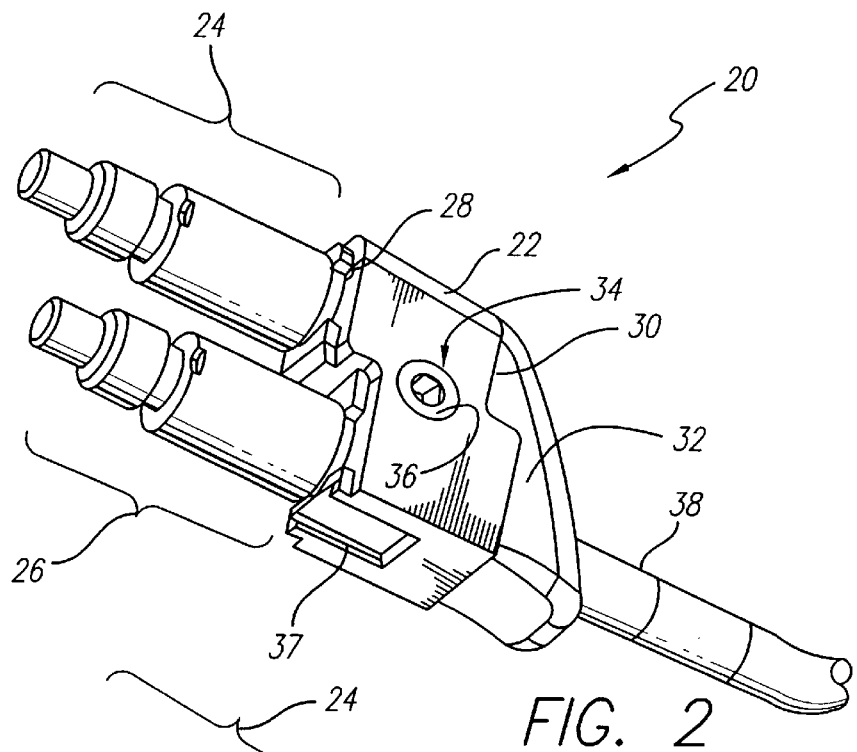
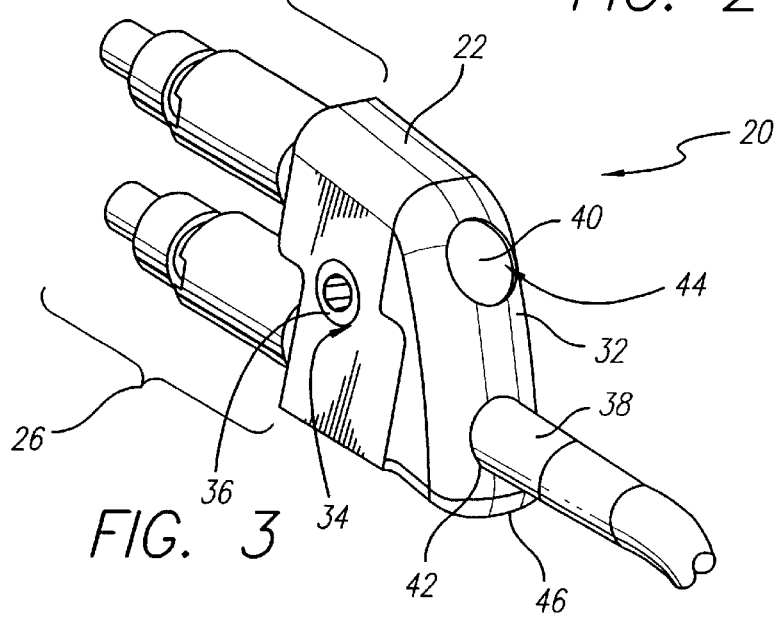

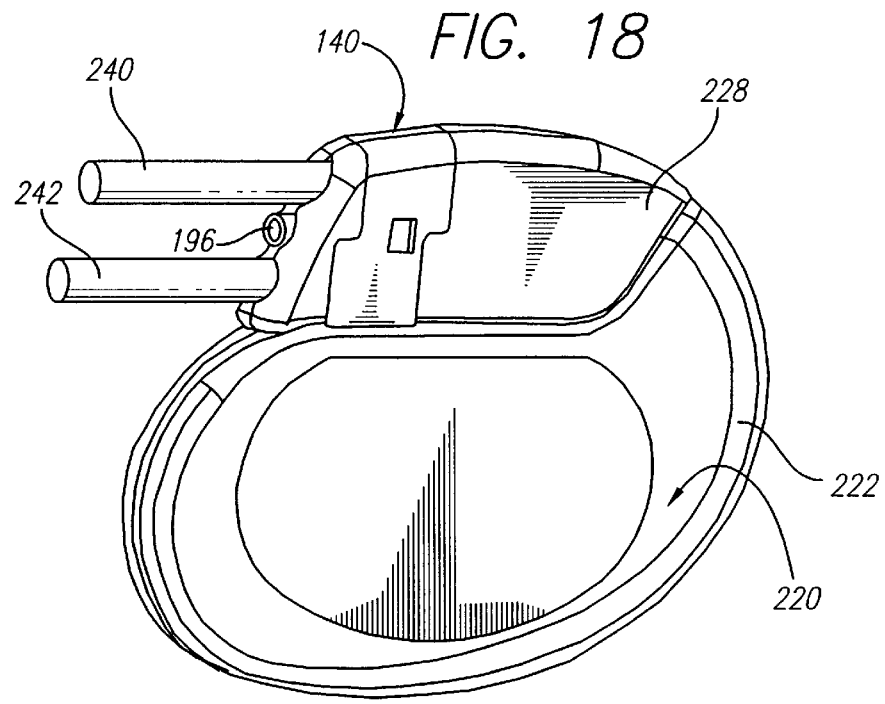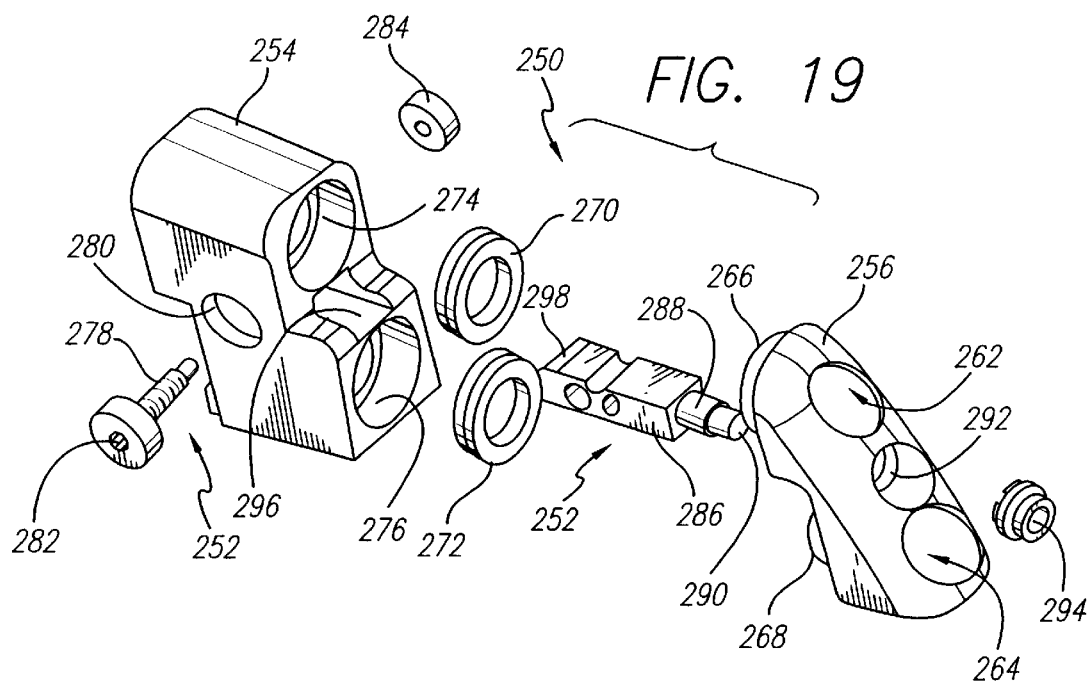

SETSCREWLESS CONNECTOR ASSEMBLY FOR IMPLANTABLE MEDICAL DEVICES

CROSS-REFERENCE TO RELATED APPLICATION

This application claims the benefit of Provisional Application Ser. No. 60/017,807, filed May 13, 1996.

FIELD OF THE INVENTION

The present invention relates generally to connector assemblies for receiving implantable leads to connect such leads to electronic circuits within an implantable medical device, such as a cardiac pacemaker, and more particularly to a connector assembly in which one or more implantable leads are fixed and sealed within lead receptacles therein.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart via an external connector assembly having lead-receiving receptacles. The appended claims are not intended to be limited, however, to any specific example or embodiment described herein.

Cardiac pacemakers, and other implantable medical devices such as cardiac defibrillators, are hermetically packaged to isolate the device from the body environment. Such devices require that electrical signals be passed between the packaged device and its external connectors, without compromising the hermeticity of the package. Depending on the configuration of the implantable device, there may be multiple electrical paths required between the device and its external connectors. These paths must be electrically and mechanically integrated with the device to provide a safe, long-term connector assembly which does not compromise the hermetic package.

Typically, a hermetic housing feedthrough electrically couples the electronic circuits to a connector assembly. The feedthrough assembly extends through the hermetically sealed outer wall of the housing and into the connector assembly so as to couple the electronic circuits within the housing to lead-receiving receptacles within the connector assembly. Each lead has one or more terminals, typically in the form of pin and one or more conductive rings. When inserted into a receptacle of connector assembly, corresponding contacts within the receptacle come into contact with the terminals on the lead so as to couple the lead to the electronic circuits within the implantable device via the feedthrough assembly. Typically, the lead is fixed or secured within the lead receptacle by one or more setscrews or other securing devices within the lead receptacle. Needless to say, it is imperative that good electrical contact be made between the lead and the connector assembly. At the same time, the connector assembly must be capable of releasing the lead from the lead receptacle during a subsequent surgical procedure.

An example of a connector assembly for receiving a lead is provided by U.S. Pat. No. 4,278,093 of Lafortune et al., which patent issued Jul. 14, 1981, and is entitled "Interchangeable Pacemaker Connector For Leads." In the particular connector assembly described in the '093 patent, the turning of a screw forces a flared end of a collet onto an electrode of a lead.

It is known in prior art connector assemblies to make electrical connection to one or more terminals on the lead by various different connector assemblies including a setscrew, a spring or a compliant electrical contact. It is also known to use a prefabricated connector assembly to hold the electrical contacts together with a series of nonconductive spacers which are made from plastic. The resulting connector subassembly is attached to the pacemaker, or other implantable device, by fixturing it over the pacemaker and having epoxy molded around the subassembly. Alternatively, the connector subassembly may be inserted into a pre-molded connector top and bonded to the pacemaker.

In those prior art connector assemblies in which the lead is fixed within the lead receptacle using a setscrew, the setscrew is often threaded into a connector block within the connector assembly. When the screw is advanced, it comes into physical contact with the pin terminal of the lead. The resulting physical connection is often used as the electrical contact as well. However, this can present one or more problems. For example, the lead is sometimes damaged by the force produced when the setscrew is tightened. Such damage must be controlled, inasmuch as the life of the lead is often longer than that of the pacemaker. Additionally, setscrews in prior art connector assemblies have a history of stripping out of the threaded block. Particularly where relatively small setscrews are used, the threads, or the hex flats, may strip. To minimize or eliminate such problems, setscrews of a certain minimum physical size are necessary. The result is often a hump on the side of the connector assembly as the physical size of the pacemaker and its connector assembly are reduced.

A further problem of prior art connector assemblies relates to the frequent desire or necessity that the terminals be insulated from body fluids. The setscrew and the setscrew block must be insulated from bodily fluids. One solution has been use of a silicone seal, called a septum. The septum forms an insulation barrier between the setscrew and bodily fluids. However, the septum must permit a wrench to pass through it so that the screw can be tightened. Frequently, the septum is damaged by the wrench, with loss of the insulation barrier being a possible result.

Accordingly, it would be desirable to provide a connector assembly for securing or fixing a lead within a lead receptacle in a manner which does not damage either the lead or the receptacle and which permits the lead to be easily removed and then reused where desired. Such connector assembly should also seal against the entry of bodily fluids.

It would also be desirable to provide a connector assembly using relatively small and compact parts which do not require enlargement of the connector assembly or the presence of septums or other protrusions therefrom.

It would still further be desirable to provide a connector assembly which includes a pre-fabricated subassembly having spaces and terminal receptacles therein which may be held in place during epoxy casting for providing a connector top design of modular form.

SUMMARY OF THE INVENTION

Briefly stated, the present invention provides a setscrewless connector assembly which utilizes an actuator mechanism to lock and seal a lead inserted into a lead receptacle. The actuator mechanism forms a part of the connector assembly which may be mounted on the top of a pacemaker or other implantable device such as by use of a dovetail mounting connector assembly. Connector subassemblies containing the lead receptacles are pressed into the connector assembly for support and for handling of the connector assembly in modular fashion. This permits conductive ribbons to be attached to the connector bore assemblies, prior to casting. The resulting connector assembly can be tested, stored or installed on a pacemaker, with minimal fixturing.

In actuator mechanisms, according to the invention, an annular recess within the lead receptacle is provided with an annular seal of deformable material. The actuator mechanism may be moved into a "lock" position to deform the annular seal against the lead and thereby fix the lead in place and form a seal around the lead. The actuator mechanism may also be moved to an "unlock" position, permitting removal of the lead from the lead receptacle. One or more connector subassemblies, which form the lead receptacles, are pressed into a molded support adapted to be mounted, such as by the dovetail mount, to the top of the pacemaker. The molded support includes an actuator and a plunger mounted at an end opposite the connector bore assemblies and movable between first and second positions to define the lock and unlock positions of the actuator. The plunger has an annular portion for engaging each annular seal to selectively compress the seal against a lead seated within the lead receptacle, to thereby fix the lead in place and form a seal around the lead.

In a first embodiment of a connector assembly according to the invention, a pair of connector bore assemblies, each forming a lead receptacle therein, are mounted within a molded support so as to extend outwardly from a back end of the molded support. A plunger disposed adjacent an opposite front end of the mold support has a pair of annular lip portions extending therefrom. A cam operated actuator mechanism moves the plunger between first and second positions along an axis of elongation of the connector assembly to selectively compress a pair of lead lock seals of annular, ring-like configuration and disposed within annular recesses at the front end of the molded support against leads inserted in the lead receptacles, when the plunger is moved into the first or "lock" position. The opposite second or "unlock" position of the plunger decompresses the lead lock seals to permit removal of the leads from the lead receptacles. The cam operated actuator mechanism of the first embodiment includes a cam actuator rotatably mounted within a transverse aperture extending through the molded support. A cam retainer affixed to the opposite end of the cam actuator maintains the cam actuator in place. The cam actuator interacts with a cam slide that is slidably disposed within a longitudinal slot in the molded support to move the plunger between the lock and unlock positions. One end of the cam slide extends from the molded support and is coupled to the plunger. Adjacent the opposite end of the cam slide is a slot which terminates in an aperture through which the cam actuator extends to the cam retainer. An offset camming portion of the cam actuator resides within the slot so as to slide the cam slide axially within the slot in the molded support and thereby move the plunger between the lock and unlock positions, in response to rotation of the cam actuator. The cam slide has a pair of limit surfaces on opposite sides of the slot which are engaged by a lobe extending therefrom. This defines the lock and unlock positions.

The cam actuator has a hex-shaped opening therein for receiving a tool such as a torque wrench. A unidirectional torque wrench may be employed to rotate the cam actuator into the lock position. In this direction, the torque wrench limits the torque applied so as to prevent breaking the stop connector assembly. However, when rotating in an opposite direction into the unlock position, the torque is not limited and the resistance of such things as interim tissue growth may be overcome.

A second embodiment of a connector assembly according to the invention is similar to the first embodiment except for the details of the actuator mechanism. In the second embodiment, a screw rotatably journaled within an aperture extending along the central axis of the molded support extends through an aperture in the plunger where it terminates in a hex driver having a tool-receiving opening therein. An opposite end of the screw is received within a threaded block disposed within an opening extending transversely through the molded support. The hex driver engages an annular recess in the plunger, so that rotation of the hex driver by a torque wrench or other tool advances the screw into the threaded block. This draws the plunger toward the molded support, so that the annular lip portions of the plunger compress the lead lock seals within the annular recesses of the molded support. This fixes in place leads inserted into the lead receptacles, while at the same time sealing such receptacles from body fluids. Rotation of the hex driver in an opposite direction withdraws the screw from the threaded block so as to release the plunger and decompress the lead lock seals, permitting removal of the leads from the lead receptacles. A retainer clip disposed within the transverse opening in the molded support on an opposite side of the threaded block from the plunger engages an end portion of the screw to prevent removal of the plunger from the molded support. A cylindrical collar may be disposed within the apertures in the molded support and the plunger to facilitate bidirectional displacement of the plunger. The collar will push against the plunger when opening, thereby disengaging the plunger and decompressing the lead lock seals.

The design of the screw operated actuator mechanism of the second embodiment provides for application of a predetermined amount of force to the lead lock seals, since there is variability in the displacement of the plunger. By using a torque wrench to rotate the hex driver of the screw, for example, the annular lip portions of the plunger compress the lead lock seals with up to a predetermined amount of torque set in the torque wrench. This controls the amount of force which is applied to the lead lock seals. Accordingly, for leads of different sizes or configurations, a predetermined amount of force can still be exerted against the leads seated within the lead receptacles.

A third embodiment of a connector assembly according to the invention is similar to the first embodiment except for the details of the actuator mechanism. In the third embodiment, the cam actuator of the first embodiment is replaced by a toothed pinion which is rotatably mounted within a transverse aperture extending through the molded support. A retainer affixed to the opposite end of the pinion maintains the pinion in place. A hex-shaped opening in the pinion receives a tool such as a torque wrench, to provide a side actuated connector assembly in the manner of the first embodiment. The pinion interacts with a slide having a toothed slot therein and forming a rack. As in the case of the cam slide of the first embodiment, the rack is slidably disposed within a longitudinal slot in the molded support to move the plunger between lock and unlock positions. One end of the rack extends from the molded support and is coupled to the plunger. The toothed slot is located adjacent an opposite end of the rack, and receives the pinion therein. The teeth of the pinion engage the teeth of the toothed slot within the rack. Consequently, when the pinion is rotated, the rack is caused to slide and thereby move the plunger between the lock and unlock positions.

As in the case of the first embodiment, the hex-shaped opening of the pinion receives a torque wrench or other tool to provide a side actuated connector assembly. This type of actuation is preferred over the front actuation of the second embodiment in which the tool must be inserted into the end of the screw actuator between a relatively closely spaced pair of leads. During implant of the front actuated design, the physician must actuate the mechanism by turning the torque wrench while both leads are in place. The leads may obstruct the physician's ability to actuate the mechanism. In addition, during explant, fibrotic growth will have formed between the leads, obstructing the physician's ability to disengage the mechanism. A side actuated connector assembly avoids these problems.

At the same time, the rack and pinion actuator mechanism of the third embodiment provides stepped displacement and force throughout the travel of the slidable rack. The manner in which the teeth of the pinion engage the teeth of the slidable rack defines a plurality of stopping locations along the travel of the rack, providing high resolution. When the force reaches the desired amount during actuation, the torque wrench torque-limits, allowing the actuator mechanism to stop at the most recently past stopping location. When the rack is moved all the way to the fully open position, the pinion "free spins" within the toothed slot of the rack, thereby preventing damage which can occur when excessive torque is applied in the case of those embodiments having hard stops.

In the first embodiment, the displacement of the cam slide is determined by the cam actuator and is fixed. Therefore, the retention force varies with the diameter and hardness of the leads. For a given hardness, the force increases with increasing lead diameter. The force can vary non-linearly with displacement, so that an extraordinarily high force can be exerted on leads of large diameter. Consequently, some compliance may be desirable, and this is accomplished by a fourth embodiment of a connector assembly according to the invention.

The fourth embodiment is similar to the first embodiment, except that the cam slide is provided with compliance. The compliance may be provided by fashioning a portion of the cam slide adjacent the end thereof, which is attached to the plunger, as a spring. Although the portion of the cam slide in contact with the cam actuator is displaced a fixed amount, the portion of the cam slide in contact with the plunger undergoes somewhat less displacement as a result of the compliance of the spring. This additional compliance helps to maintain a more linear relationship with deflection. Alternatively, the compliance can be provided by a compliant nut used to couple the cam slide to the plunger.

BRIEF DESCRIPTION OF THE DRAWINGS

Further objects, advantages and features of the invention will become apparent from the detailed description of the preferred embodiments when read in conjunction with the accompanying drawings, in which:

FIG. 1 is a perspective view of a bipolar lead;

FIG. 2 is a perspective view of a first embodiment of a connector assembly in accordance with the invention;

FIG. 3 is a different perspective view of the connector assembly of FIG. 2;

FIG. 18 is a different perspective view of the cardiac pacemaker and connector assembly of FIG. 17 with a pair of leads shown installed in the connector assembly;

FIG. 19 is an exploded perspective view of a third embodiment of a connector assembly in accordance with the invention;

DESCRIPTION OF THE PREFERRED EMBODIMENTS

Figure 4:
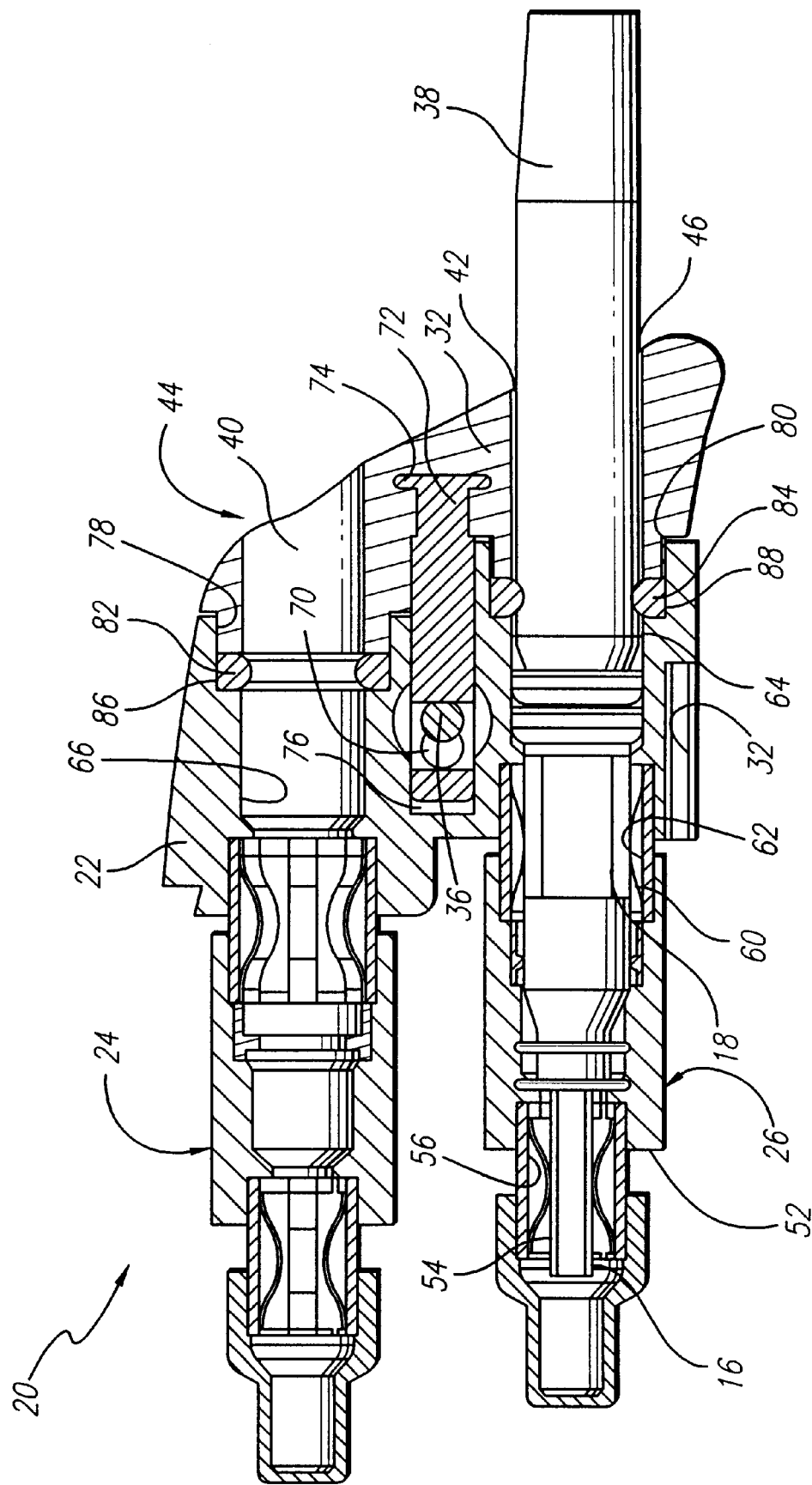
FIG. 4 is a sectional view of the connector assembly of FIG. 2.

FIG. 1 shows a conventional bipolar lead 10. For cardiac pacemaker applications, the lead 10 comprises a transvenous pacing lead. Depending upon the type of cardiac pacemaker, there may be one or two of the leads 10 corresponding to single-chamber or dual-chamber pacemakers. Also, while the lead 10 of FIG. 1 is of the bipolar variety, there are unipolar leads which contain but a single electrode. The particular bipolar lead 10 of FIG. 1 is shown as a common example of a cardiac pacemaker lead, and is useful in understanding the connector assemblies described hereafter. It should be understood, however, that other lead designs can be used in accordance with the invention.

The bipolar lead 10 shown in FIG. 1 has a connector end 12 provided with a spaced pair of terminals 16, 18. In conventional connector assemblies, a pin terminal 16 may be engaged by a setscrew, and a ring terminal 18 may be engaged by a spring or other resilient conductive member, to make electrical contact to the connector end 12 of the lead 10 within the connector assembly. Seal rings 14 and 15 are disposed on opposite sides of the ring terminal 18. The terminals 16 and 18 are connected to electrodes at an opposite end of the lead 10 (not shown) by internal conductors. For convenience of illustration, only a portion of the lead 10 is shown in FIG. 1. With the lead 10 mounted within a lead receptacle of a connector assembly, the terminals 16 and 18 are electrically coupled to the electronic circuits within the attached cardiac pacemaker, or other implantable device.

FIG. 2 shows a connector assembly 20 in accordance with a first embodiment of the invention. The connector assembly 20 of FIG. 2 includes a molded support 22 having a pair of connector bore assemblies 24 and 26 mounted at a back end 28 thereof. An opposite front end 30 of the molded support 22 has a plunger 32 disposed thereat. As described in detail hereafter, the connector assembly 20 includes a cam operated actuator mechanism 34, of which the plunger 32 forms a part. The actuator mechanism 34 includes a cam actuator 36, rotation of which moves the plunger 32 between opposite first and second positions to selectively lock or unlock one or more leads seated in lead receptacles within the connector assembly 20. The connector assembly 20 includes a dovetail mount 37 at the bottom of the molded support 22 to facilitate mounting of the connector assembly 20 on the top of a cardiac pacemaker, as described hereafter.

FIG. 3 is a different view of the connector assembly 20 of FIG. 2 in which a proximal end of a lead 38 is shown inserted within the connector assembly 20. As described in detail hereafter, the plunger 32 is provided with a spaced apart pair of cylindrical plunger chambers 40 and 42 having central axes which are parallel to each other. The plunger chambers 40 and 42 form the front ends of a pair of lead receptacles 44 and 46. The lead 38 is shown inserted within the lead receptacle 46. From the plunger chambers 40 and 42, the lead receptacles 44 and 46 extend through cylindrical support chambers within the molded support 22 to the elongated hollow interiors of the connector bore assemblies 24 and 26. Within each lead receptacle 44 and 46, the central axis of the plunger chamber defines the central axis of the connecting cylindrical support chamber within the molded support 22 and the elongated hollow interior of the connector bore assembly 24 or 26.

Because the support 22 is molded of a material such as polysulfone, the connector bore assemblies 24 and 26, which are of essentially conventional configuration, can be press fitted into place within the molded support 22. When so assembled, the molded support 22 and the included connector bore assemblies 24 and 26 form a modular portion of the connector assembly 20, which may be mounted on a cardiac pacemaker using the dovetail mount 37. The plunger 32, which may also be made of polysolfone or other appropriate material, is movably joined to the molded support 22 in a manner described hereafter.

FIG. 4 is a sectional view of the connector assembly 20. In FIG. 4, the lead 38 is shown (in plan view) seated within the lead receptacle 46. The lead 38 is a bipolar lead having a configuration similar to the lead 10 shown in FIG. 1. As such, the lead 38 has a pin terminal 16 at a proximal end 52 (i.e., proximal to pacemaker), which is engaged by electrical contacts 54 within an elongated hollow interior 56 of the connector bore assembly 26. The proximal end 52 also includes a ring terminal 18 engaged by electrical contacts 60 within the elongated hollow interior 62. The lead receptacle 46 is comprised of the plunger chamber 42 within the plunger 32, the cylindrical support chamber 64 within the molded support 22, and the elongated hollow interior 62 of the connector bore assembly 26. The plunger chamber 42, the cylindrical support chamber 64 and the elongated hollow interior 62 have a common central axis which defines the central axis of the lead receptacle 46. In similar fashion, the lead receptacle 44 is comprised of the plunger chamber 40 within the plunger 32, a cylindrical support chamber 66 within the molded support 22, and an elongated hollow interior 62 within the connector bore assembly 24. The plunger chamber 40, the cylindrical support chamber 66 and the elongated hollow interior 68 have common central axes which define the central axis of the lead receptacle 44.

As previously noted, fixation and sealing of leads, such as the lead 38 shown in FIG. 4, is accomplished using the cam actuator 36. The cam actuator 36 is shown in section in FIG. 4 as it resides within an aperture 70 in a cam slide 72. As shown in FIG. 4, the cam slide 72 has an enlarged end portion 74 thereof fixedly disposed within the plunger 32. Consequently, sliding movement of the cam slide 72 within a slot 76 in the molded support 22 moves the plunger 32 toward or away from the molded support 22. The cam actuator 36 and the cam slide 72 are made of titanium alloy or other appropriate strong, lightweight material.

Figure 5:
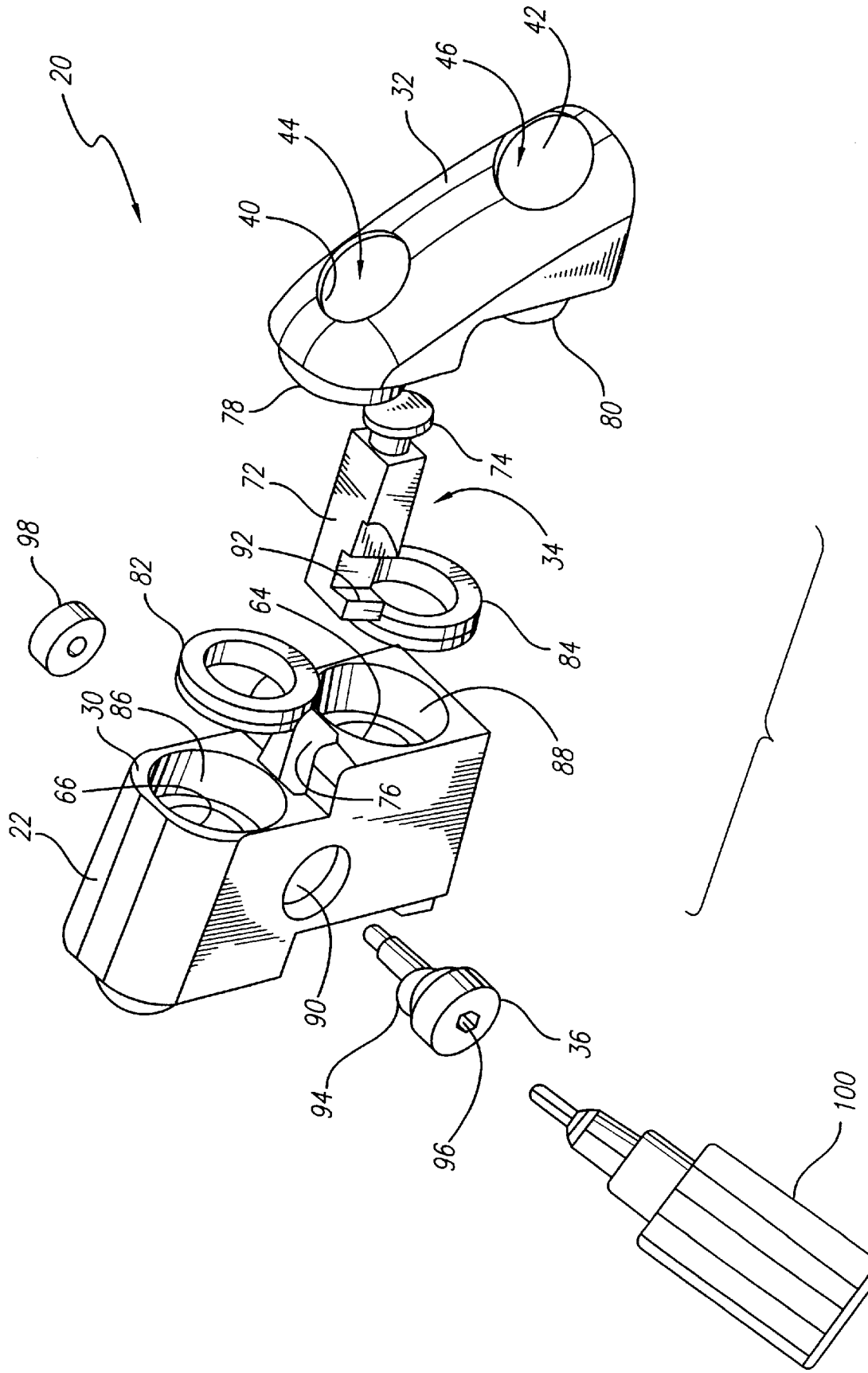
FIG. 5 is an exploded perspective view of the molded support, the plunger and the cam operated actuator mechanism of the connector assembly of FIG. 2.

As described hereafter in connection with FIG. 5, rotation of the cam actuator 36 (FIG. 4) produces sliding movement of the cam slide 72 within the slot 76 (FIG. 4). Movement of the cam slide 72 in a direction to the left, as viewed in FIG. 4, causes upper and lower annular lip portions 78 and 80 extending from the plunger 32 to compress lead lock seals 82 and 84 which are seated within annular recesses 86 and 88 at the front end 30 of the molded support 22. The annular recesses 86 and 88 surround the entrances to the cylindrical support chambers 66 and 64, respectively, within the molded support 22. The lead lock seals 82 and 84 are ring-like in shape, and comprise O-rings in the present example. They are made of appropriate resilient, elastomeric material such as silicone. Compression of the lead lock seals 82 and 84 by the annular lip portions 78 and 80 of the plunger 32 presses the lock lead seals 82 and 84 against leads inserted within the lead receptacles 44 and 46 so as to fix and seal the leads therein.

FIG. 4 shows the lead 38 installed within the lead receptacle 46. Consequently, compression of the lead lock seal 84 by the annular lip portion 80 presses the lead lock seal 84 against the lead 38. This secures or fixes the lead 38 within the lead receptacle 46. It also seals the lead receptacle 46 to prevent entry of body fluids therein. Movement of the plunger 32 to the right as viewed in FIG. 4 decompresses the lead lock seals 82 and 84, so that leads installed within the lead receptacles 44 and 46 can be removed. As described hereafter, bidirectional sliding movement of the cam slide 72 between a "lock" position to the left and an "unlock" position to the right is controlled by rotation of the cam actuator 36.

FIG. 5 shows the molded support 22, the plunger 32 and the actuator mechanism 34 in exploded fashion. The cam actuator 36 is rotatably mounted within an aperture 90 extending transversely through the molded support 22. As previously noted in connection with FIG. 4, the cam slide 72 is slidably disposed within the slot 76 in the molded support 22. The slot 76 intersects the aperture 90 at right angles. The cam slide 72 has a slot 92 on one side thereof from which the aperture 70 (FIG. 4) extends through the thickness of the cam slide 72. The cam actuator 36 extends through the aperture 70 in the cam slide 72 so as to dispose an offset camming portion 94 within the slot 92 in the cam slide 72. Because the camming portion 94 is offset, rotation of the offset camming portion 94 within the slot 92 causes sliding movement of the cam slide 72 within the slot 76.

The cam actuator 36 is provided with a hex aperture 96. At an end of the cam actuator 36 opposite the hex aperture 96, a cam retainer 98 is attached to the cam actuator 36. The cam retainer 98, which like the cam actuator 36 and the cam slide 72 may be made of titanium alloy or similar material, retains the cam actuator 36 within the aperture 90, while at the same time permitting rotation thereof.

The hex aperture 96 within the cam actuator 36 permits engagement of the cam actuator 36 by a hex-shaped tool such as a torque wrench 100 shown in FIG. 5. Rotation of the cam actuator 36 in a clockwise direction eventually moves the cam slide 72 into a "lock" position in which the lead lock seals 82 and 84 are compressed to fix and seal leads within the lead receptacles 44 and 46. From the lock position, rotation of the cam actuator 36 in a counterclockwise direction slides the cam slide 72 to the right until it eventually reaches an "unlock" position in which the lead lock seals 82 and 84 are uncompressed and leads within the lead receptacles 44 and 46 may be removed. As described hereafter, rotation of the cam actuator 36 beyond the lock or unlock positions is prevented by a lobe on the cam actuator 36 which engages opposite limit surfaces.

While any tool having a hex-shaped end can be used to rotate the cam actuator 36, the torque wrench 100 is preferred because the amount of torque applied thereby can be limited in one or both directions of rotation of the cam actuator 36. Preferably, the torque wrench 100 is adjusted to limit the torque in the lock direction but not in the unlock direction. By limiting the torque in the clockwise or lock direction, the cam actuator 36 is rotated to and seated at the lock position without danger of damaging or breaking the cam actuator 36 or the associated parts. In the counterclockwise or unlock direction, however, it may be desirable not to limit the applied torque. Because the cardiac pacemaker may be installed in a patient for a significant number of years before removal of leads from the connector assembly 20 becomes necessary, interim tissue growth may impede the unlocking process. In that event, enough force must be applied to accomplish unlocking.

Figure 6:
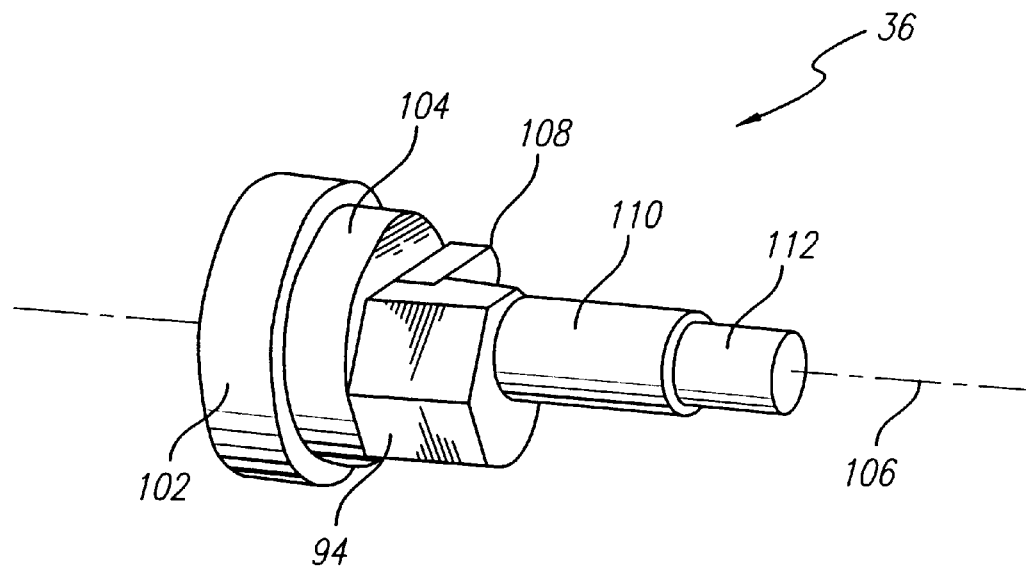
FIG. 6 is a perspective view of the cam actuator shown in FIG. 5.

FIG. 6 shows the cam actuator 36 with the offset camming portion 94. As shown therein, the cam actuator 36 includes an enlarged head 102 of cylindrical configuration at one end thereof. The head 102 has the hex aperture 96 shown in FIG. 5 therein. Disposed between the head 102 and the offset camming portion 94 is a cylindrical member 104 having a diameter slightly smaller than that of the head 102. The offset camming portion 94, which extends from an axis of rotation 106 of the cam actuator 36 in offset or eccentric fashion, includes a lobe 108 extending from a portion thereof. As described hereafter, the lobe 108 engages opposite limit surfaces to stop rotation of the cam actuator 36 at the lock and unlock positions. A cylindrical shaft 110 which extends from the offset camming portion 94 along the axis of rotation 106 terminates in a shaft portion 112 of reduced diameter for receiving the cam retainer 98 shown in FIG. 5.

Figure 7:
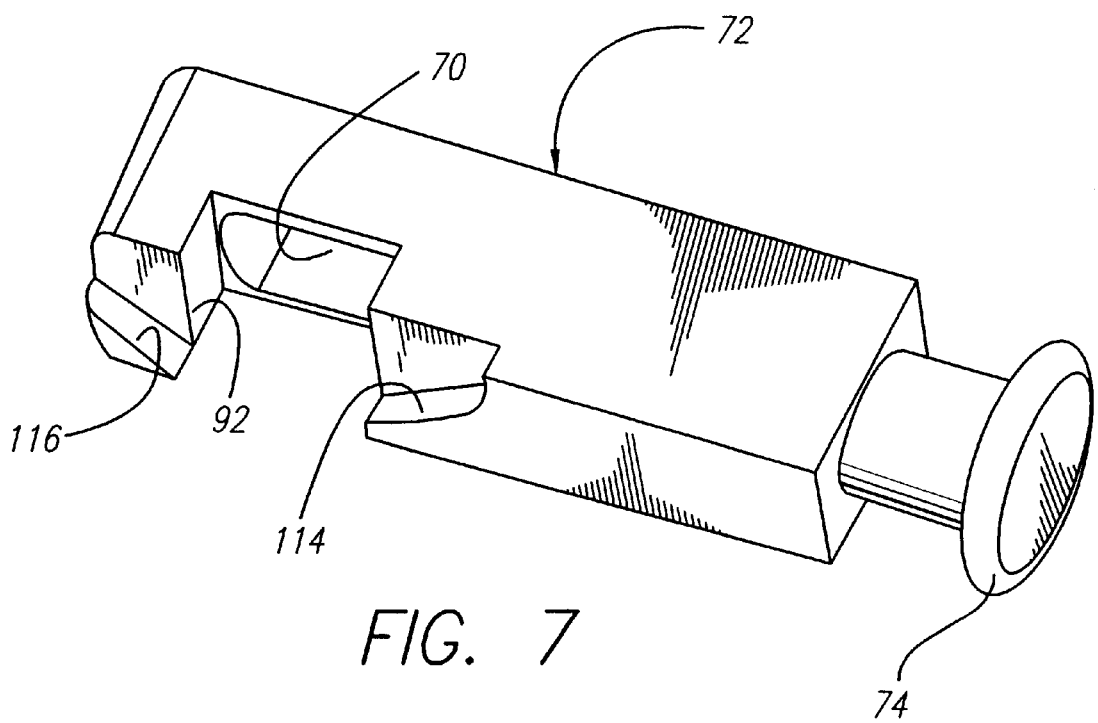
FIG. 7 is a perspective view of the cam slide shown in FIG. 5.

The cam slide 72 is shown in detail in FIG. 7. As shown therein, the cam slide 72 is of elongated, generally rectangular configuration and terminates at one end thereof in the enlarged end portion 74 which is embedded within the plunger 32. An opposite end of the cam slide 72 is provided with the slot 92 from which the aperture 70 extends through the thickness of the cam slide 72. As shown in FIG. 7, the aperture 70 is of generally oval cross-sectional configuration to permit sliding movement of the cam slide 72 within the slot 76 (FIG. 5) relative to the cylindrical shaft 110 of the cam actuator 36 which resides within the aperture 70. The front of the slot 92 is configured to provide opposite limit surfaces 114 and 116. Engagement of the limit surface 114 by the lobe 108 of the cam actuator 36 defines the lock position. Conversely, the limit surface 116 is engaged by the lobe 108 to define the opposite unlock position.

Figure 8:
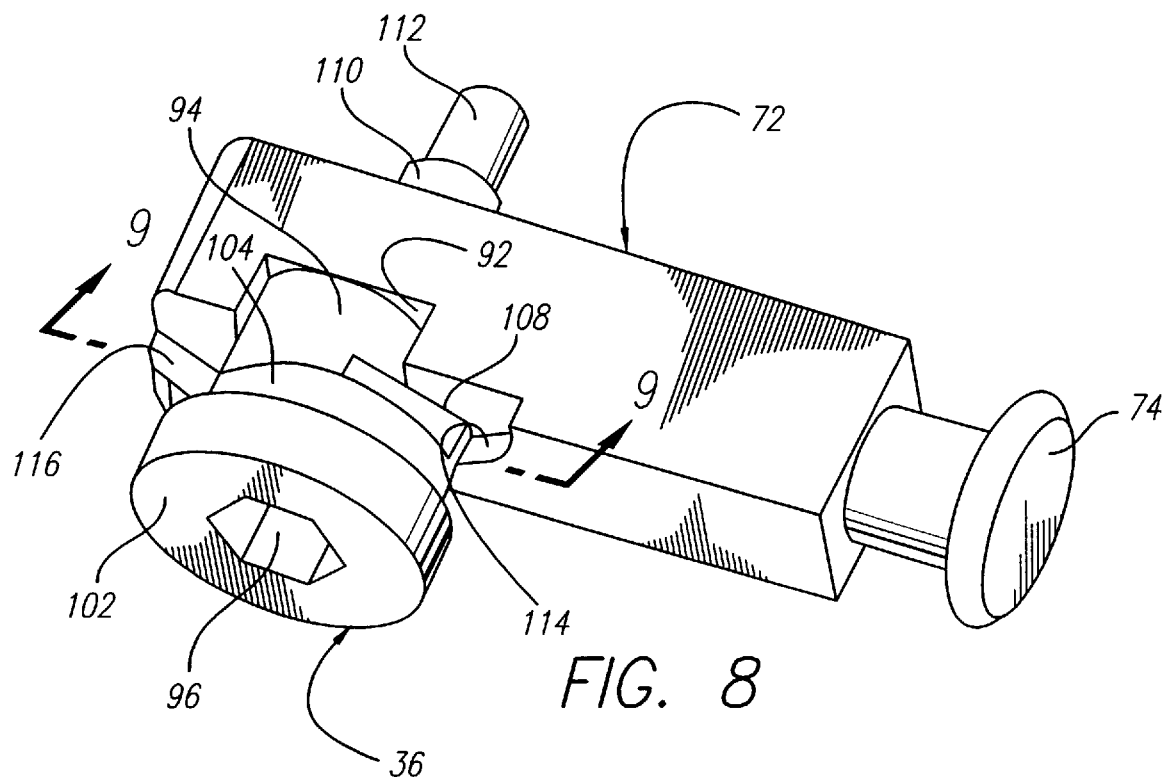
FIG. 8 is a perspective view of the cam actuator and the cam slide of FIGS. 6 and 7 respectively, showing the manner in which the cam actuator interacts with the cam slide.

FIG. 8 shows the cam actuator 36 installed within the slot 92 and the aperture 70 of the cam slide 72. In FIG. 8, the cam actuator 36 has been rotated into the lock position such that the lobe 108 engages the limit surface 114. The offset camming portion 94 has moved the cam slide 72 into the extreme left position, so that the lead lock seals 82 and 84 are compressed against leads within the lead receptacles 44 and 46 to fix and seal such leads. If the torque wrench 100 is then placed in the hex aperture 96 within the head 102, and the cam actuator 36 is rotated in a counterclockwise direction, the offset camming portion 94 slides the cam slide 72 to the right to decompress the lead lock seals 82 and 84 and thereby unfix and unseal the leads within the lead receptacles 44 and 46. The cam actuator 36 is stopped in the unlock position by engagement of the limit surface 116 by the lobe 108.

Figure 9:
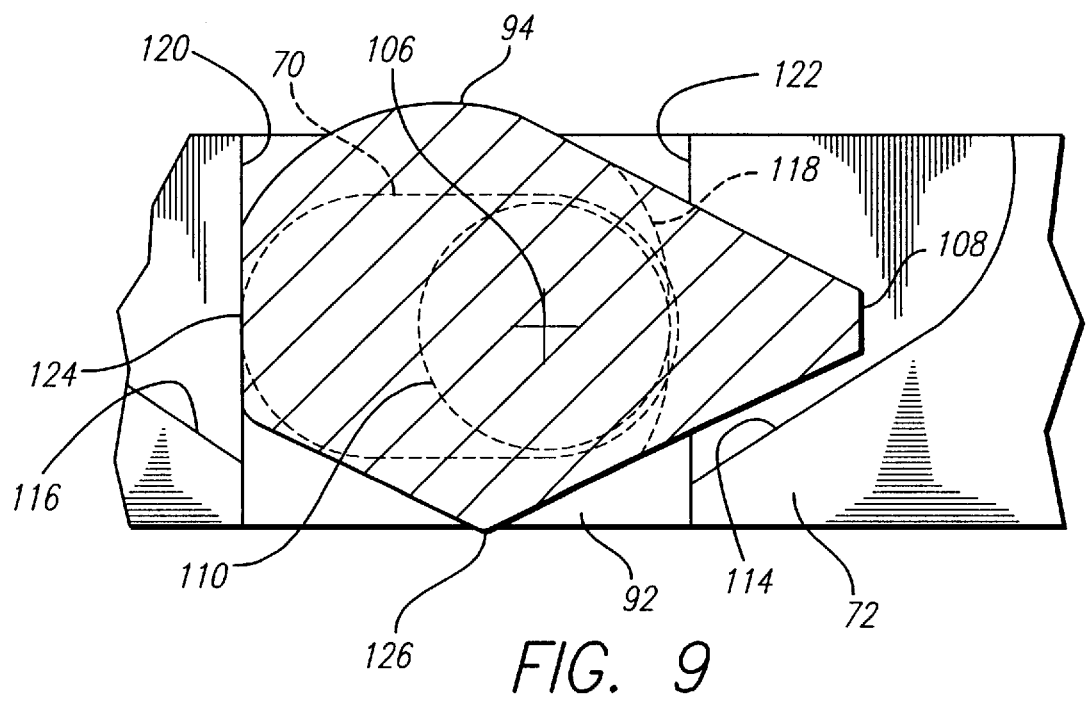
FIG. 9 is a sectional view of a portion of FIG. 8 illustrating further details of an offset camming portion and a lobe of the cam actuator and opposite limit surfaces of the cam slide.

FIG. 9 is a cross-sectional view of a portion of FIG. 8 taken along the line 9—9 thereof. The cylindrical shaft 110 of the cam actuator 36 is shown in dotted outline. The axis of rotation 106 of the cam actuator 36 is represented by crossed lines in FIG. 9. The aperture 70 in the cam slide 72 is represented by a dashed line. The position of the offset camming portion 94 in FIG. 9 corresponds to the position shown in FIG. 8 in which the cam actuator 36 is essentially in the lock position. As seen in FIG. 9, the lobe 108 touches or nearly touches the limit surface 114. The portion of the offset camming portion 94 behind the lobe 108 is represented by the dotted line 118 in FIG. 9.

As seen in FIG. 9, the slot 92 in the cam slide 72 has left and right surfaces 120 and 122 respectively. With the cam actuator 36 in the lock position, as shown in FIG. 9, a relatively flat portion 124 of the outer surface of the offset camming portion 94 engages the surface 120 to hold the cam slide 72 in the lock position. If the cam actuator 36 is then rotated in a counterclockwise direction, the flat portion 124 moves away from the left surface 120. Shortly after that, a ridged portion 126 of the offset camming portion 94 engages the right surface 122 to continue movement of the cam slide 72 to the right. Eventually, a relatively flat portion 124 engages the right surface 122. At the same time, the lobe 108 engages the limit surface 116 to stop the cam actuator 36 in the unlock position. Rotation of the cam actuator 36 in the clockwise direction then reverses the process, with the flat portion 124 moving away from the right surface 122 and the flat portion 124 eventually engaging the left surface 120.

In the first embodiment of the connector assembly 20 of FIGS. 2–9, the cam actuator 36, and thus the cam slide 72, are moved between predetermined opposite limits defining the lock and unlock positions. Consequently, the plunger 36 with its annular lip portions 78 and 80 is moved between predetermined opposite positions. Therefore, the extent of compression of the lead lock seals 82 and 84 on leads mounted within the lead receptacles 44 and 46 is dependent upon a number of factors including the size of the lead lock seals 82 and 84, the size of the annular recesses 86 and 88 in which the lead lock seals 82 and 84 reside, and also the external diameters of the leads. For lead lock seals and annular recesses of a given size, the lead lock seal will be compressed onto the outer surface of a lead of smaller diameter with less force. Consequently, the force of compression of the lead lock seals on the leads is dependent upon and will vary with such things as lead diameter. It may be desirable for certain applications to provide a fixing and sealing connector assembly in which the compressed lead lock seals exert a relatively constant force on the leads. Such a connector assembly is represented by a second embodiment which will now be described, with reference being made to FIG. 10.

The second embodiment of a connector assembly 140 in accordance with the invention is shown in FIGS. 10–14. The various parts of the connector assembly 140 are similar to those of the connector assembly 20 of FIGS. 2–9. The principal differences lie in the details of the actuator mechanism, which are described hereafter. Whereas the connector assembly 20 of FIGS. 2–9 utilizes the cam actuator 36, the connector assembly 140 of FIGS. 10–14 utilizes a threaded screw actuator capable of exerting a constant force on the leads.

Figure 10:
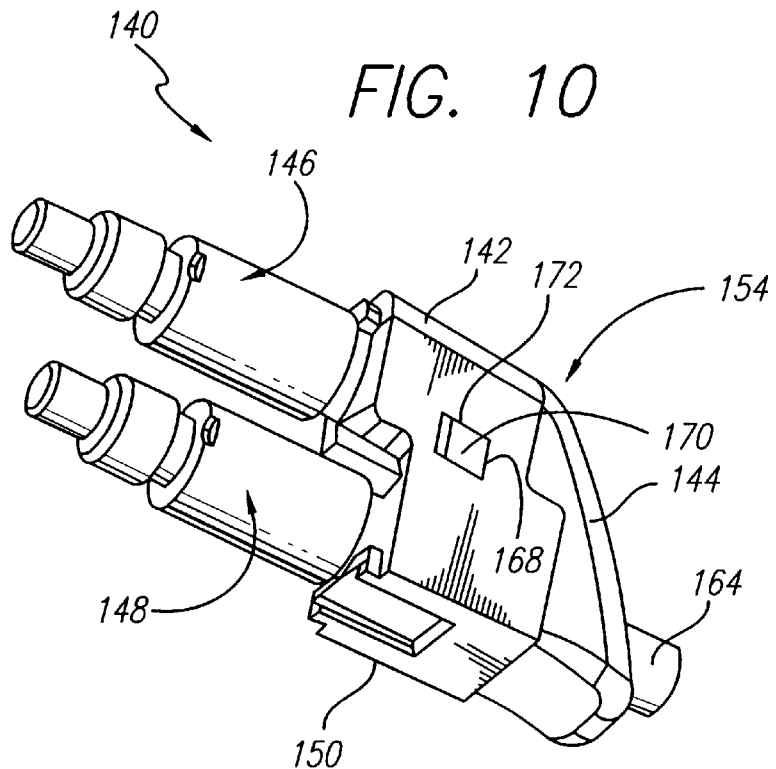
FIG. 10 is a perspective view of a second embodiment of a connector assembly in accordance with the invention.
Figure 11:
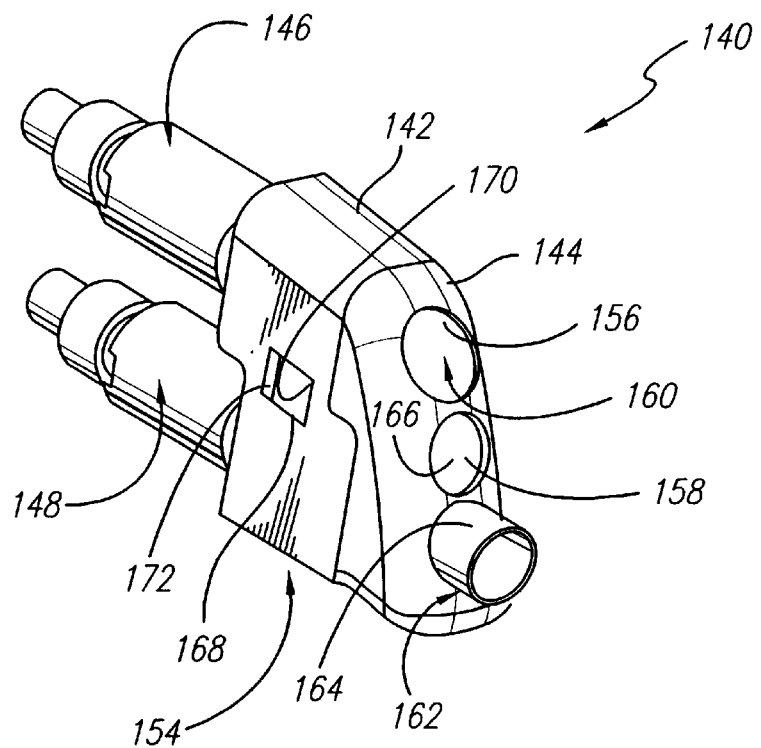
FIG. 11 is a different perspective view of the connector assembly of FIG. 10.

As shown in FIGS. 10 and 11, the connector assembly 140 includes a molded support 142, a plunger 144 and a pair of connector bore assemblies 146 and 148. A dovetail mount 150 at the bottom of the molded support 142 facilitates mounting of the connector assembly 140 on top of a cardiac pacemaker. The molded support 142 and the plunger 144 house an actuator mechanism 154 which is described in detail in connection with FIGS. 13 and 14. The plunger 144 is provided with a pair of plunger chambers 156 and 158 forming the entrances to a pair of lead receptacles 160 and 162. A portion of a lead 164 is shown within the lead receptacle 162.

The actuator mechanism 154 of the connector assembly 140 includes a screw actuator 166 which extends through the plunger 144 and into the molded support 142, as described hereafter. A transverse aperture 168 extends through the molded support 142, and seats a threaded block 170 and a retainer clip 172 therein.

Figure 12:
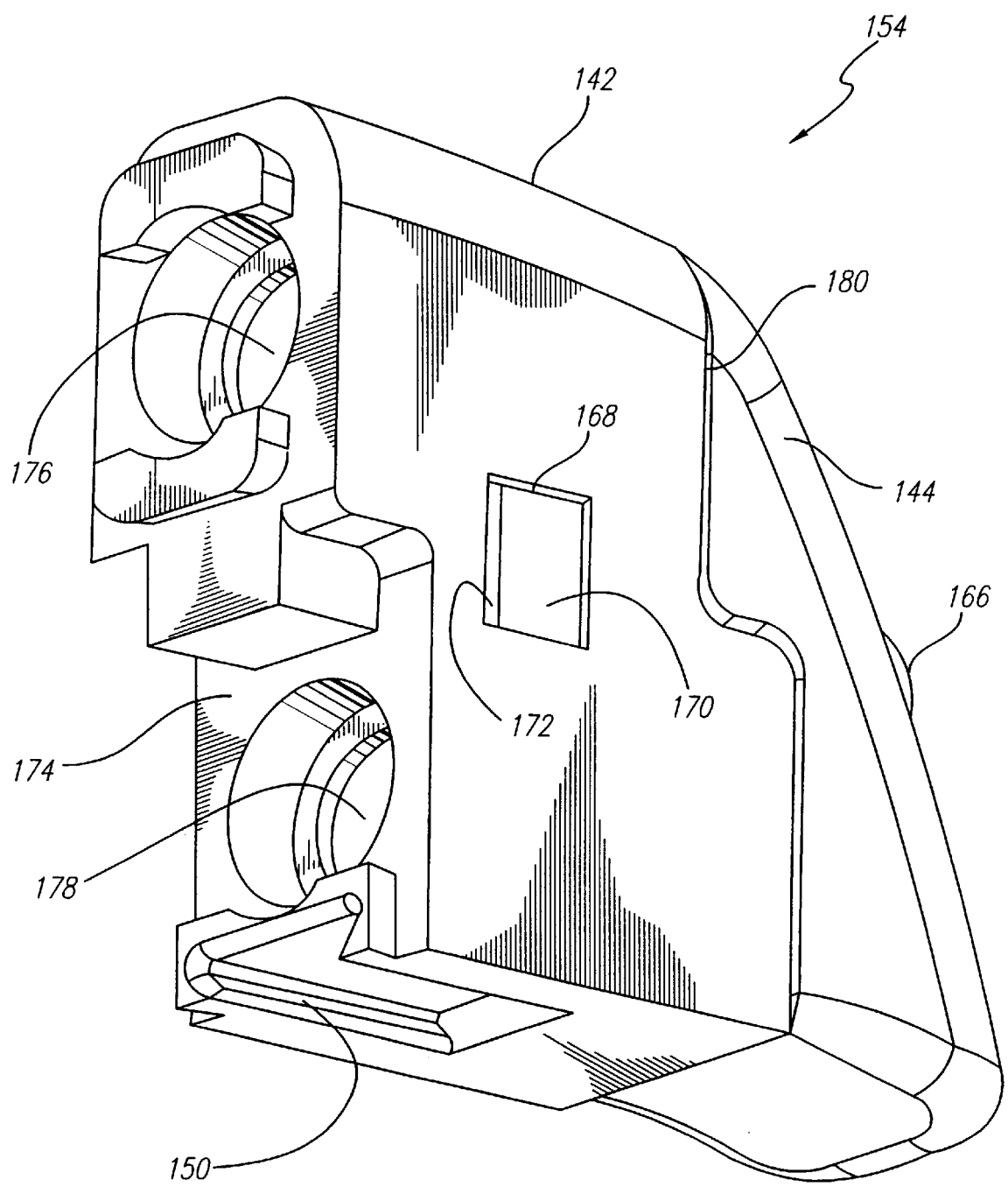
FIG. 12 is a perspective view of the molded support and plunger of the connector assembly of FIG. 10.

FIG. 12 shows the molded support 142 and the plunger 144. Extending to a back end 174 of the molded support 142 are a pair of cylindrical support chambers 176 and 178. The cylindrical support chamber 176 couples to and has a common central axis with the plunger chamber 156 at a front end 180 of the molded support 142 and with an elongated hollow interior of the connector bore assembly 146 at the back end 174, to form the lead receptacle 160. In similar fashion, the cylindrical support chamber 178 couples to the plunger chamber 158 at the front end 180 of the molded support 142 and to an elongated hollow interior of the connector bore assembly 148 at the back end 174 of the molded support 142, to form the lead receptacle 162. As in the case of the connector assembly 20 of FIGS. 2–9, the connector bore assemblies 146 and 148 can be press fitted into the cylindrical support chambers 176 and 178 at the back end 174 of the molded support 142 to mount the connector bore assemblies therein.

Figure 13:
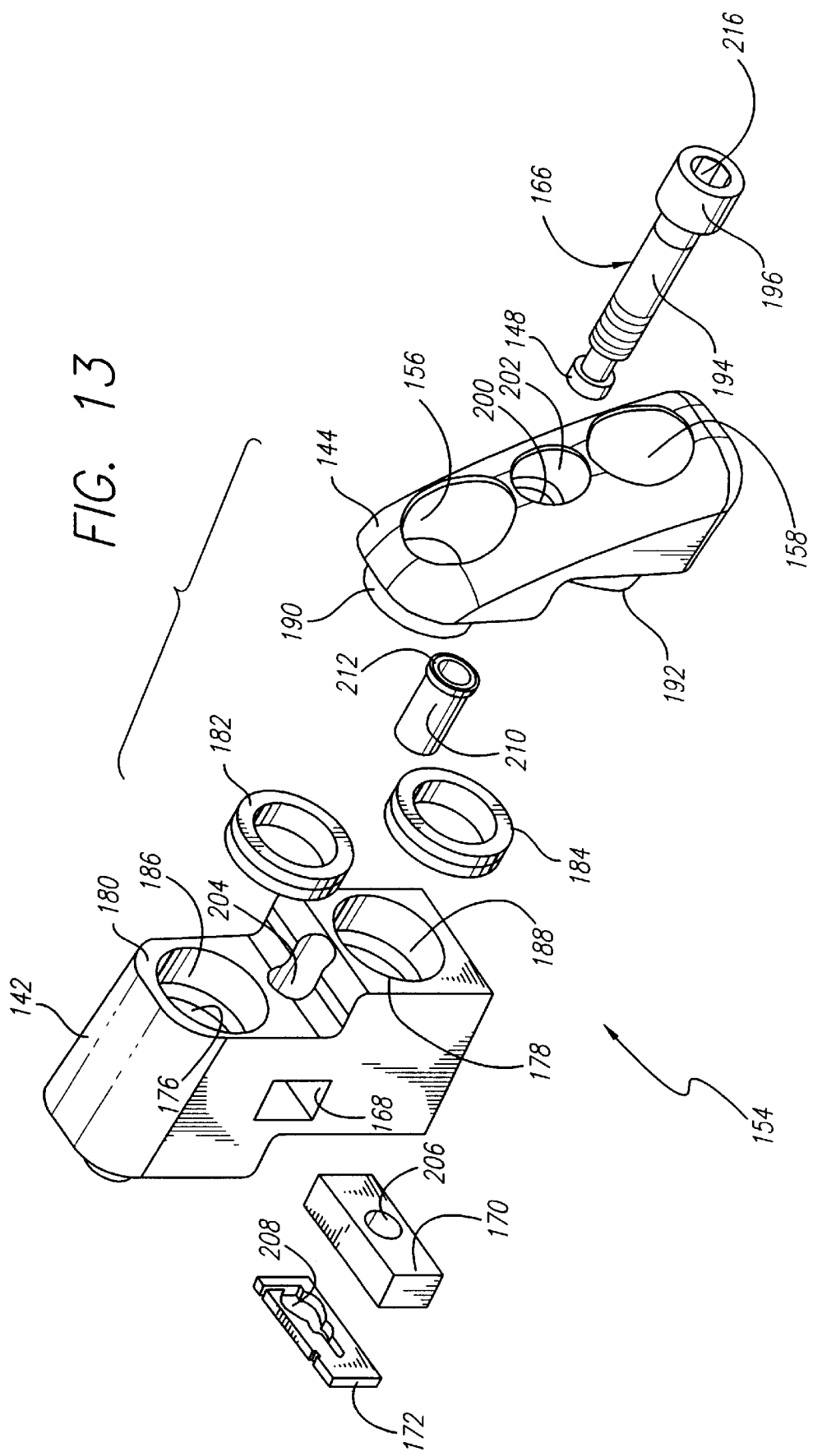
FIG. 13 is an exploded perspective view of the molded support and plunger as shown in FIG. 12.

FIG. 13 is an exploded perspective view of the molded support 142 and the plunger 144 shown in FIG. 12. A pair of lead lock seals 182 and 184 seated within annular recesses 186 and 188 at the front end 180 of the molded support 42 are selectively compressed and decompressed by annular lip portions 190 and 192 of the plunger 144, as the plunger 144 is moved toward and away from the molded support 142.

As shown in FIG. 13, the screw actuator 166 is comprised of a shaft 194 threaded along a portion of the length thereof and having an enlarged hex driver 196 at one end thereof and a cylindrical keeper 198 at an opposite end thereof. The screw actuator 166 is journaled within an aperture 200 extending through the plunger 144 between the plunger chambers 156 and 158, and having an annular recess 202 therein against which the enlarged hex driver 196 resides. The annular recess 202 limits movement of the screw actuator 166 therethrough, thereby maintaining the plunger 144 mounted at the front end 180 of the molded support 142. From the plunger 144, the shaft 194 of the screw actuator 166 extends into an aperture 204 in the molded support 142. The aperture 204 which has a central axis coinciding with that of the aperture 200 in the plunger 144 forms an extension of the aperture 200 within the plunger 144. The aperture 204 is disposed between the cylindrical support chambers 176 and 178 in the molded support 142 and intersects with the transverse aperture 168 at a right angle within the molded support 142.

The threaded block 170 has a threaded aperture 206 extending therethrough. The retainer clip 172 has an aperture 208 therein which is larger adjacent one end of the retainer clip 172 than at a location adjacent the opposite end of the retainer clip 172. A collar 210 of hollow cylindrical configuration and having an enlarged lip 212 at one end thereof is disposed within portions of the aperture 200 in the plunger 144 and the aperture 204 in the molded support 142 so as to rotatably receive a portion of the shaft 194 therein.

When the actuator mechanism 154 is assembled, the threaded block 170 and the retainer clip 172 are seated, side-by-side, in the transverse aperture 168. The shaft 194 of the screw actuator 166 extends into the aperture 204 in the molded support 142 so that the threaded portion thereof is seated within the threaded aperture 206 in the threaded block 170. Initially, the retainer clip 172 is only partially inserted into the transverse aperture 168 so that the keeper 198 at the end of the shaft 194 passes through the enlarged part of the aperture 208 therein. Thereafter, movement of the retainer clip 172 to a position completely within the transverse aperture 168 moves the smaller portion of the aperture 208 into a position between the shaft 194 and the keeper 198. If the threaded portion of the shaft 194 is rotated all the way out of the threaded aperture 206 in the threaded block 170, the keeper 198 engages the retainer clip 172 to prevent removal of the plunger 144 from the molded support 142.

Figure 14:
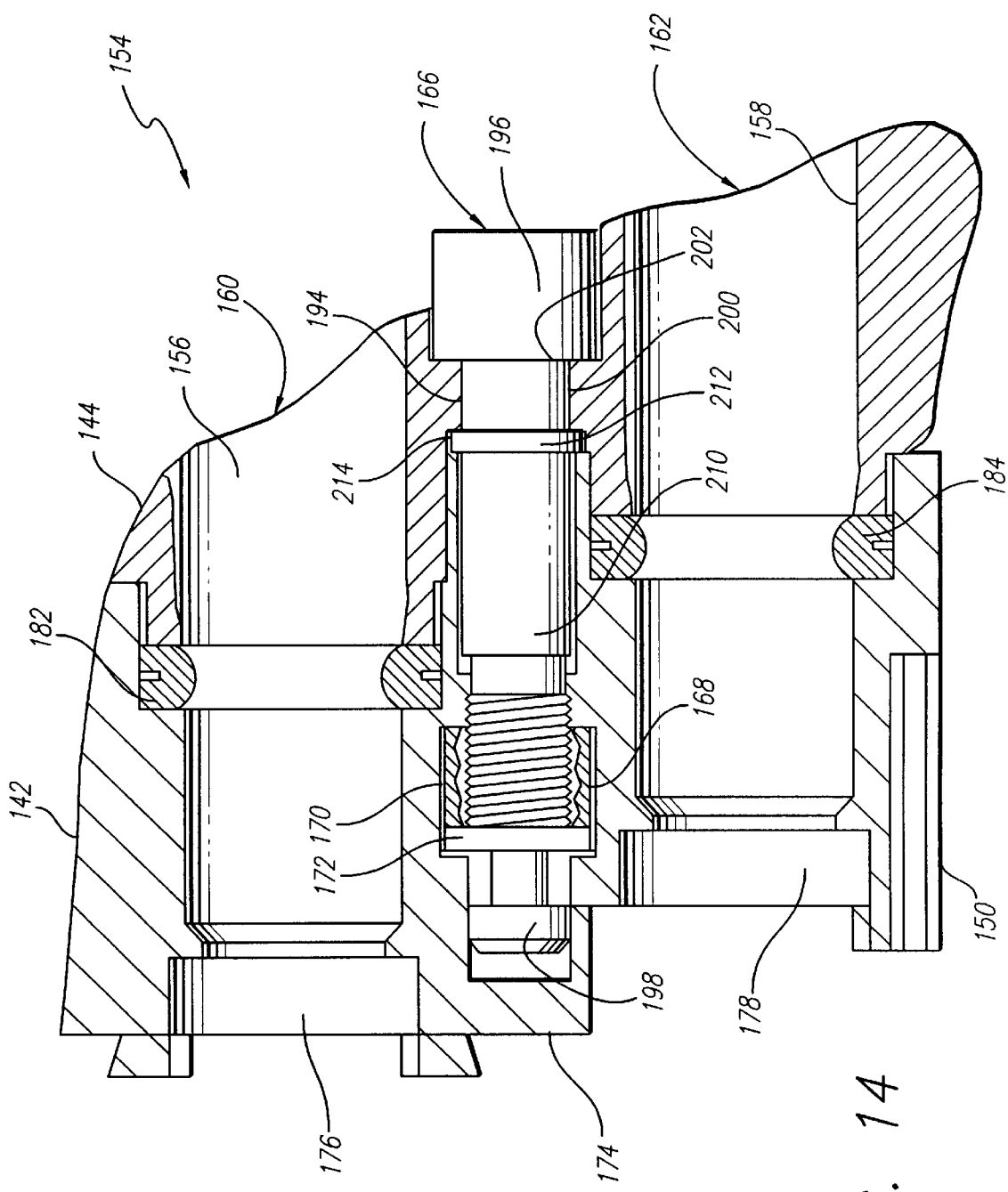
FIG. 14 is a sectional view of the molded support and plunger shown in FIG. 12.

The sectional view of the molded support 142 in FIG. 14 shows the screw actuator 166 (in plan view) seated in place and threaded into the threaded block 170 in the transverse aperture 168. A portion of the shaft 194 is rotatably received within the collar 210 to facilitate the free rotation of the shaft 194 at the interface of the molded support 142 and the plunger 144. The enlarged lip 212 of the collar 210 seats against an annular shoulder 214 within the aperture 200 in the plunger 144. As shown in FIG. 13, the hex driver 196 at the end of the shaft 194 has a hex aperture 216 therein for receiving the hexagonal end of a torque wrench or other tool. The torque wrench 100 shown in FIG. 5 is an example of a tool which may be used to rotate the shaft 194 by engagement within the hex aperture 216. Rotation of the shaft 194 in a clockwise direction as seen in FIG. 13 advances the threaded portion of the shaft 194 into the threaded block 170, thereby moving the plunger 144 in the direction of the molded support 142. The annular lip portions 190 and 192 of the plunger 144 compress the lead lock seals 182 and 184 within the annular recesses 186 and 188 and onto leads inserted in the lead receptacles 160 and 162 to fix and seal the leads therein. Rotation of the shaft 194 in an opposite or counterclockwise direction as seen in FIG. 13 withdraws the threaded part of the shaft 194 from the threaded block 170 so as to permit movement of the plunger 144 away from the molded support 142 and thereby decompress the lead lock seals 182 and 184. Should the shaft 194 be rotated far enough to remove the threaded portion thereof from the threaded block 170, the retainer clip 172 engages the keeper 198 to prevent the plunger 144 being removed from the molded support 142.

In the case of the connector assembly 20 of FIGS. 2–9, the cam actuator 36 thereof provides a constant displacement of the cam slide 72 as it is moved between the lock and unlock positions. Thus, the cam slide 72 travels the same distance independent of the diameter or hardness of the inserted lead. Consequently, the retention force imparted on the lead will vary as the lead diameter and hardness thereof vary. This can be a limitation in those instances where the retention force becomes unacceptably low.

On the other hand, the screw actuator 166 of the connector assembly 140 of FIGS. 10–14 provides a constant force independent of lead diameter and hardness. As the screw 194 is rotated in a clockwise direction as seen in FIG. 13, the lead lock seals 182 and 184 come into contact with leads disposed within the lead receptacles 160 and 162. As the screw 194 continues to be rotated in this direction, the force imparted on the leads increases, as does the torque necessary to rotate the screw 194. Eventually the force imparted on the leads, as well as the torque, is at a predetermined level. If a torque wrench is being used to rotate the screw 194, the predetermined level causes the wrench to torque-limit. Therefore, as leads of different diameters and hardnesses are mounted in the lead receptacles 160 and 162, the screw 194 displaces the plunger 144 by an amount sufficient to develop a predetermined force, as determined by the torque.

As in the case of the connector assembly 20 of FIGS. 2–9, the molded support 142 and the plunger 144 of the connector assembly 140 can be made of appropriate material such as polysulfone. The lead lock seals 182 and 184 can be made of silicone. The hex driver 196, the shaft 194 and the threaded block 170 can be made of an appropriate strong, lightweight material such as titanium alloy.

Figure 15:
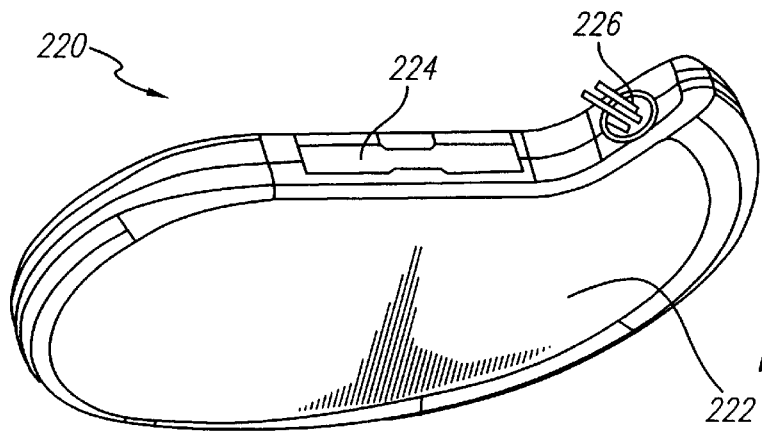
FIG. 15 is a perspective view of a cardiac pacemaker with which the connector assemblies of FIGS. 2–14 may be used.
Figure 16:
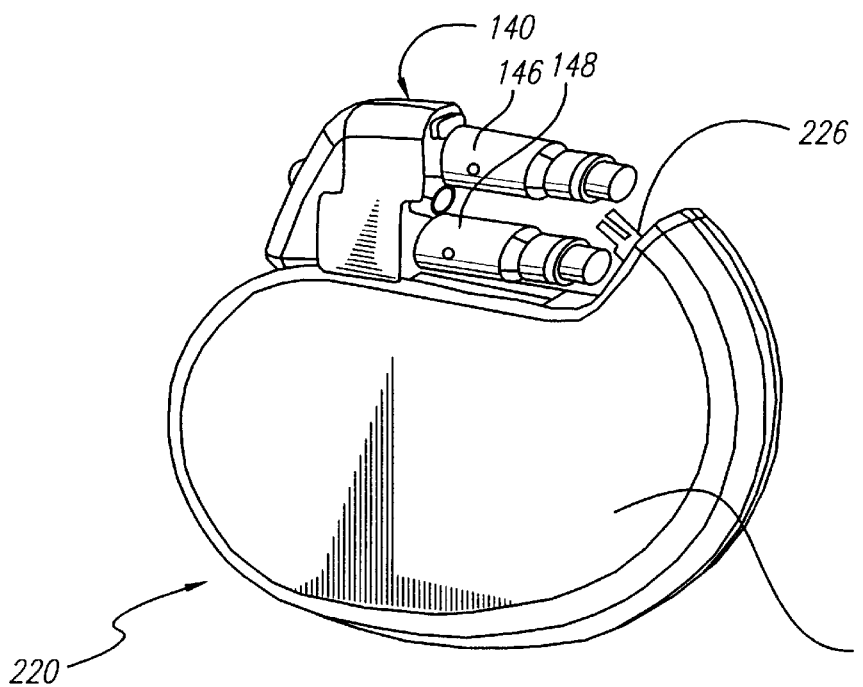
FIG. 16 is a perspective view of the cardiac pacemaker of FIG. 15 with the connector assembly of FIG. 10 mounted thereon.
Figure 17:
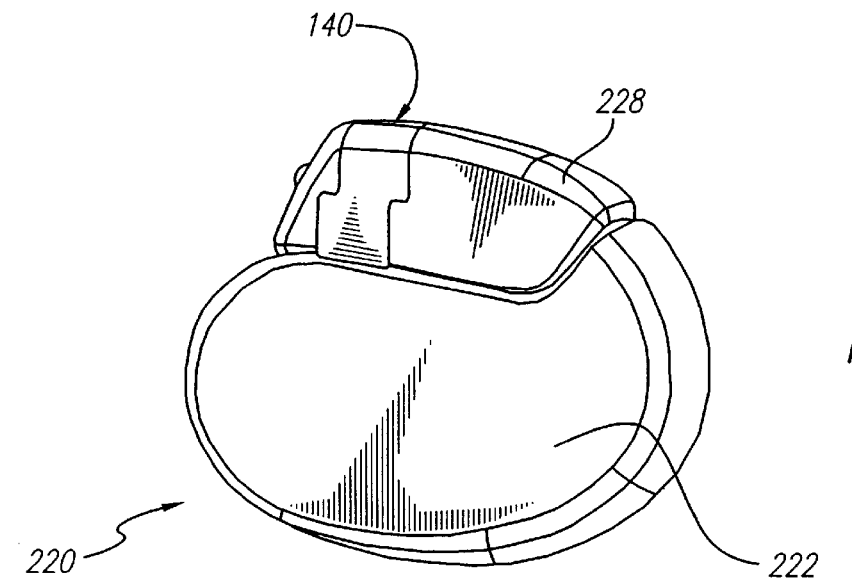
FIG. 17 is a perspective view similar to that of FIG. 16 and showing the manner in which epoxy casting can be used to encase the connector assembly at the top of the cardiac pacemaker.

FIGS. 15–17 illustrate the manner in which a connector assembly, such as the assembly 140 of FIGS. 10–14, can be assembled and installed on a cardiac pacemaker 220. The pacemaker 220 is of conventional design and includes a housing or pacer can 222 surrounding the electronic components on the inside thereof. The pacer can 222 is assembled and welded with connector braces 224 at a top edge thereof. The connector assembly 140 is assembled in the manner previously described, following which connector ribbons are attached so as to couple the pins of a feedthrough assembly 226 at a top edge of the pacemaker 220 to the connector bore assemblies 146 and 148. Next, the connector assembly 140 is slid onto the top edge of the pacemaker 220 by inserting the dovetail mount 150 into the connector braces 224 at the top edge of the pacemaker 220. The connector assembly 140 as installed in this manner is shown in FIG. 16. A quantity of epoxy 228 is then cast in place over the connector bore assemblies 146 and 148 to form an integral connector assembly structure at the top edge of the pacemaker 220, as shown in FIG. 17.

With the connector assembly 140 mounted on the pacemaker 220 and epoxy molded, as shown in FIG. 17, the connector assembly 140 is completed by inserting the lead lock seals 182 and 184 in place, inserting the threaded block 170 and the retainer clip 172 within the transverse aperture 168 and then installing the screw actuator 166.

FIG. 18 is a different perspective view of the cardiac pacemaker 220 and the connector assembly 140 of FIG. 17, showing a pair of leads 240 and 242 installed in the connector assembly 140. As previously described, the screw actuator mechanism 154 of the connector assembly 140 is operated by inserting a torque wrench or other tool in the hex driver 196 at the end of the screw actuator 166. The hex driver 196 is exposed to the outside of the connector assembly 140, at the front of the plunger 144.

As shown in FIG. 18, the hex driver 196 is positioned between the leads 240 and 242, when the leads 240 and 242 are installed in the connector assembly 140. During implant of the arrangement shown in FIG. 18, the physician inserts the leads 240 and 242 into the connector assembly 140. The physician must then actuate the connector assembly 140 by inserting a torque wrench in the hex driver 196 and turning the wrench. The leads 240 and 242 may obstruct the physician's ability to actuate the connector assembly 140. Moreover, during explant, when it is desired to remove the leads 240 and 242 from the connector assembly 140, fibrotic growth will have formed between the leads 240 and 242. Frequently, this obstructs the physician's ability to disengage the leads using a torque wrench. The physician may have to use a scalpel to remove the fibrotic tissue in the region of the hex driver 196, in order to be able to insert the torque wrench in the hex driver 196. This procedure involves risk. If the physician accidentally cuts one of the leads 240 and 242, the replacement of such lead is a significant procedure.

For this reason, a side actuated connector assembly, such as the connector assembly 20 of FIGS. 2–9, is preferred over a front actuated connector assembly, as in the case of the connector assembly 140 of FIGS. 10–18. At the same time, the connector assembly 140 of FIGS. 10–18 is advantageous in being able to provide a desired, constant force on the leads independent of displacement of the actuator mechanism. As previously pointed out, the connector assembly 20 of FIGS. 2–9 has a fixed displacement, so that the force on the leads varies with lead hardness and diameter.

A third embodiment of a connector assembly 250 in accordance with the invention is shown in FIGS. 19–24. The various parts of the connector assembly 250 are similar to those of the connector assembly 20 of FIGS. 2–9. The principal differences lie in the details of the actuator mechanism, which are described hereafter. Whereas the connector assembly 20 of FIGS. 2–9 utilizes the cam actuator 36, the connector assembly 250 of FIGS. 19–24 utilizes a rack and pinion actuator mechanism 252. The rack and pinion actuator mechanism 252 is a side actuated design, which is capable of stepped displacement and force so as to have high resolution.

As shown in FIGS. 19–24, the connector assembly 250 includes a molded support 254 and a plunger 256, which house the rack and pinion actuator mechanism 252, described in detail in connection with FIGS. 21–24. The plunger 256 is provided with a pair of lead receptacles 262 and 264. The plunger 256 is also provided with annular lip portions 266 and 268 for compressing a pair of lead lock seals 270 and 272 within annular recesses 274 and 276 at a front end of the molded support 254, as the plunger 256 is moved toward and away from the molded support 254 by the rack and pinion actuator mechanism 252.

The rack and pinion actuator mechanism 252 includes a toothed pinion 278 rotatably journaled within an aperture 280 which extends transversely through the molded support 254. The toothed pinion 278 has a hex aperture 282 at one end thereof, for actuation of the connector assembly 250 by a torque wrench or other tool. A retainer 284 is mounted on an opposite end of the pinion 278, to rotatably secure the pinion 278 within the aperture 280 in the molded support 254.

The rack and pinion actuator mechanism 252 includes an elongated rack 286 having a front end 288 thereof coupled to the plunger 256. The end 288 is coupled to the plunger 256 by a threaded portion 290 which extends through an aperture 292 within the plunger 256, between the lead receptacles 262 and 264, and which receives a threaded nut 294 thereon. With the rack 286 coupled to the plunger 256 in this fashion, sliding movement of the rack 286 within a slot 296 extending through the molded support 254 acts to compress and decompress the seals 270 and 272 within the recesses 274 and 276.

Sliding movement of the rack 286 within the slot 296 is produced by rotation of the pinion 278. The pinion 278 extends through a toothed slot 298 within a portion of the rack 286 opposite the front end 288 thereof, so that the teeth of the toothed pinion 278 engage the teeth of the toothed slot 298, as described in greater detail hereafter in connection with FIGS. 21–24.

Figure 20:
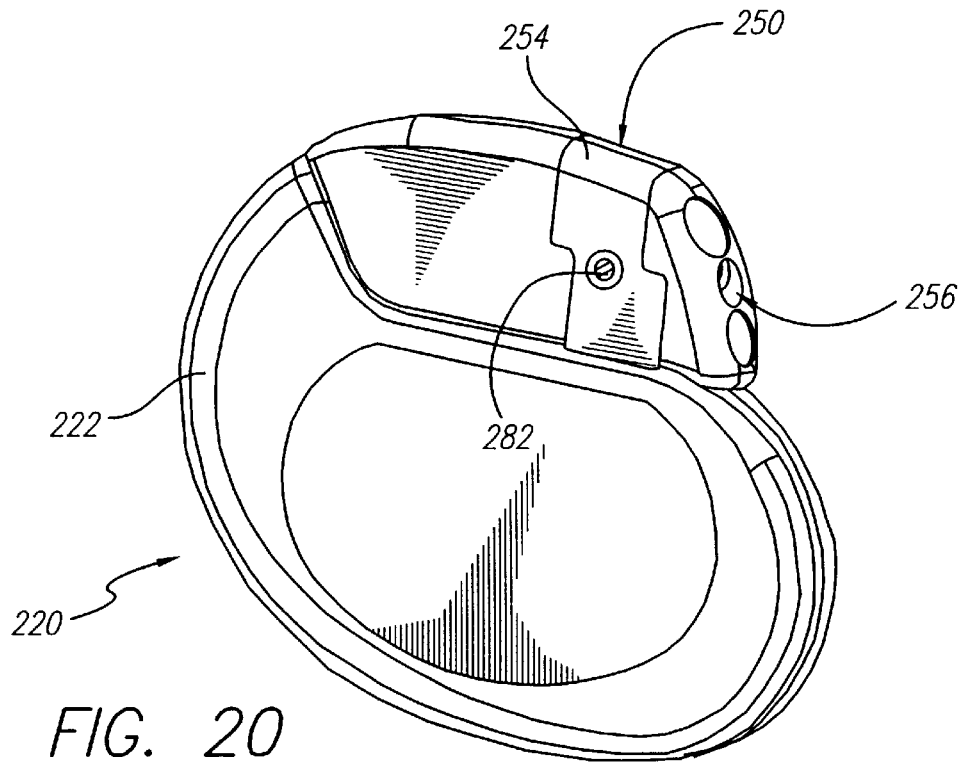
FIG. 20 is a perspective view of the cardiac pacemaker of FIG. 15 with the connector assembly of FIG. 19 mounted thereon.

FIG. 20 shows the connector assembly 250 mounted on the cardiac pacemaker 220 of FIG. 15. As shown in FIG. 20, the hex aperture 282 at the side of the molded support 254 provides for side actuation of the connector assembly 250. As previously noted, this is preferred to the front actuation of the connector assembly 140 of FIGS. 10–18.

Figure 21:
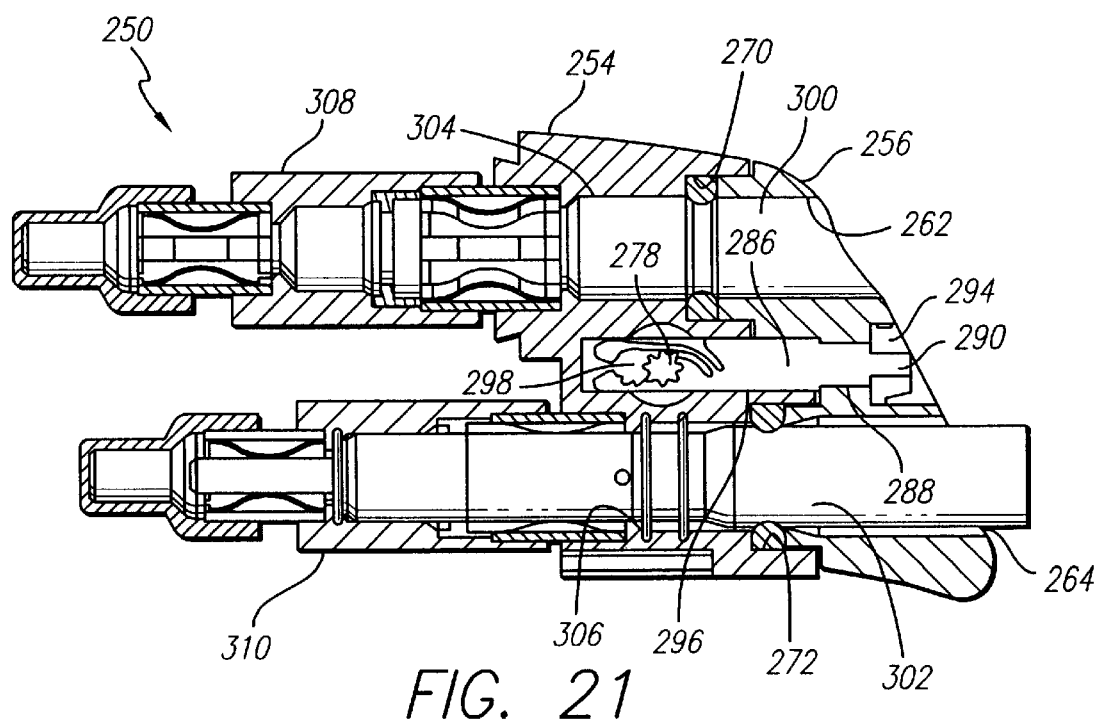
FIG. 21 is a sectional view of the connector assembly of FIG. 19.

The sectional view of FIG. 21 shows the rack 286 seated in place within the slot 296 in the molded support 254, so that the toothed pinion 278 is received within the toothed slot 298 in the rack 286. In the view of FIG. 21, the pinion 278 has been rotated to a close position, in which the plunger 256 compresses the lead lock seals 270 and 272 onto the outer surfaces of a pair of leads 300 and 302 to lock the leads in place. The leads 300 and 302, which are disposed within the lead receptacles 262 and 264 within the plunger 256, extend through cylindrical support chambers 304 and 306 within the molded support 254 and into connector bore assemblies 308 and 310, in the manner of the embodiments of FIGS. 2–18.

Figure 22:
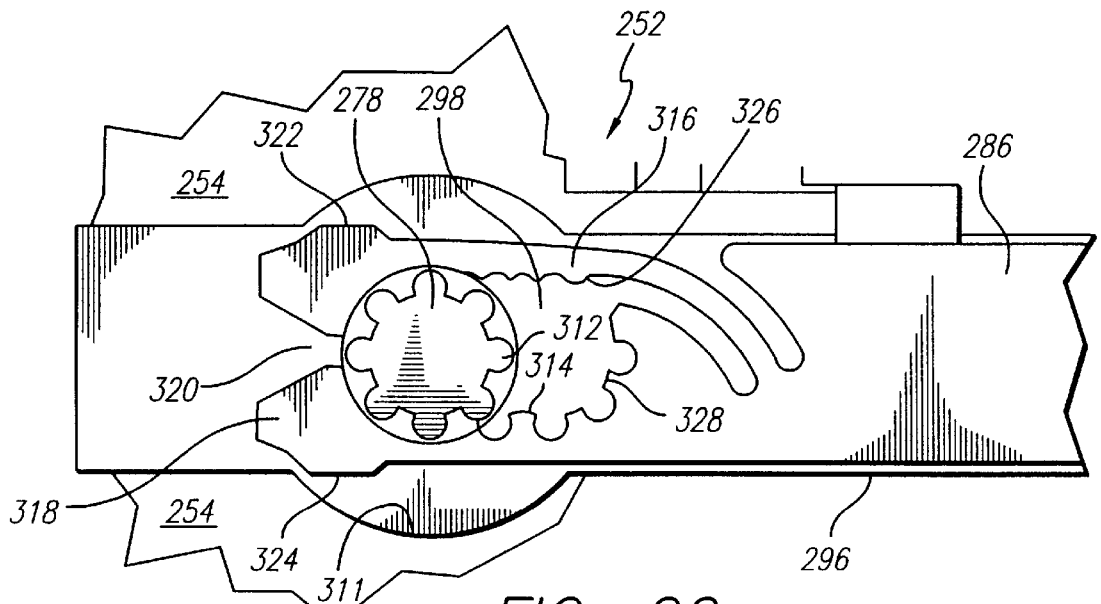
FIG. 22 is a sectional view of the slidable rack and rotatable pinion of the connector assembly of FIG. 19 with the rack in an open position.
Figure 23:
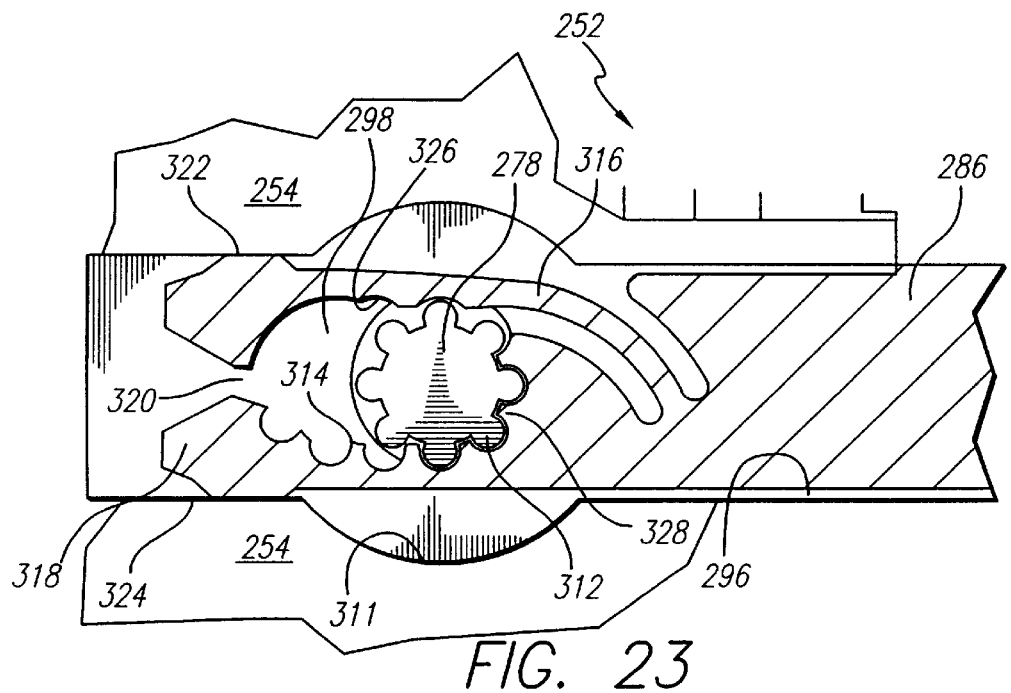
FIG. 23 is a sectional view of the slidable rack and rotatable pinion of FIG. 22 with the rack in a close position.
Figure 24:
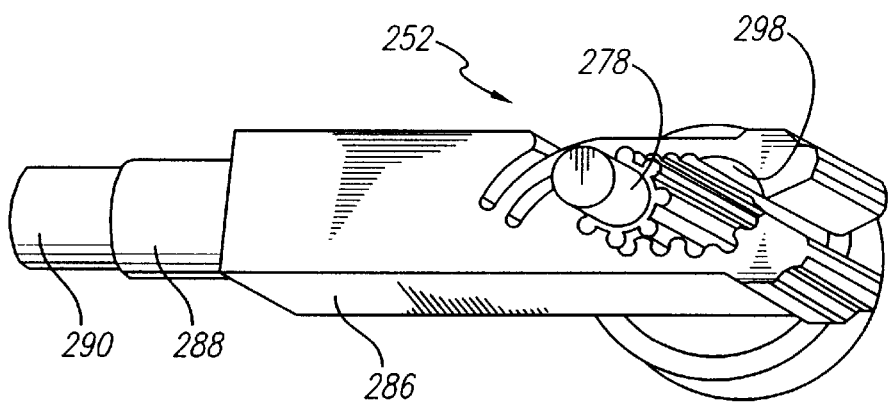
FIG. 24 is a perspective view of the slidable rack and rotatable pinion of FIG. 22.

FIGS. 22 and 23 are sectional views of the rack and pinion actuator mechanism 252 together with surrounding portions of the molded support 254. The rack 286 is disposed within the slot 296 in the molded support 254. As previously noted, the toothed pinion 278 is rotatably journaled within the aperture 280 in the molded support 254. Within the slot 296, the aperture 280 opens to a substantially larger aperture 311 which defines rounded, partially cylindrical surfaces forming recesses in the generally flat upper and lower surfaces of the slot 296.

FIG. 22 shows the rack and pinion actuator mechanism 252 in one of its opposite positions, in which the pinion 278 is at the left-hand end of the toothed slot 298. In this position, the plunger 256 is in its open position and the seals 270 and 272 are uncompressed. As described in detail hereafter, the pinion 278 is free to rotate within the toothed slot 298 of the rack 286, so that it is able to "free spin". Unlike the embodiments previously described in which excessive torque in the open direction can damage the mechanism because of the movement stops involved, continued rotation of the pinion 278 in a counterclockwise direction, as viewed in FIG. 22, allows the pinion 278 to free spin, so that no damage to the mechanism can occur.

The ability of the pinion 278 to free spin when the rack 286 is in the open position is provided for by the shape of a plurality of teeth 314 along a lower portion of the slot 298 and by the construction of the rack 286. The upper portion of the slot 298 is formed by a portion 316 of the rack 286 of long, thin configuration. The natural resilience of the material of the rack 286 allows for small amounts of movement of the portion 316 relative to an opposite portion 318 of the rack 286 which defines the lower portion of the slot 298. The portions 316 and 318 are separated by a space 320, and are respectively provided with nubs 322 and 324. When the rack 286 is in the open position shown in FIG. 22, the nubs 322 and 324 reside within the recesses provided by the large aperture 311, and the portions 316 and 318 of the rack 286 are free to be forced apart from each other. Counterclockwise rotation of the pinion 278 allows the teeth 312 thereof to ride over the upper surface of the slot 298 defined by the upper portion 316 and over several ramp shaped ones of the teeth 314 on the lower portion 318. At the same time, the upper and lower portions 316 and 318 separate from each other as necessary so that the pinion 278 free spins within the slot 298 with continued counterclockwise rotation thereof.

When it is desired to move the plunger 256 to the close position and compress the seals 270 and 272, the pinion 278 is rotated in a clockwise direction as viewed in FIG. 22. When this occurs, the teeth 312 at the outer surface of the pinion 278 mesh with the teeth 314 at the bottom portion of the toothed slot 298. This begins a sliding movement of the rack 286 to the left, as viewed in FIG. 22. As the teeth 312 of the pinion 278 mesh with the teeth 314 at the bottom portion of the slot 298, opposite ones of the teeth 312 of the pinion 278 engage a plurality of relatively small teeth or ridges 326 at the upper portion of the slot 298. The small teeth 326 catch the teeth 312 of the pinion 278 to prevent inadvertent reversal in the clockwise rotation of the pinion 278.

As the pinion 278 continues to be rotated in the clockwise direction, as viewed in FIGS. 22 and 23, using a torque wrench or other appropriate tool inserted in the hex aperture 282, the rack 286 advances to the left along the slot 296. The nubs 322 and 324 of the upper and lower portions 316 and 318 of the ramp 286 engage the upper and lower surfaces of the slot 296, and this limits the separation of the upper and lower portions 316 and 318. At the same time the resilience of the thin upper portion 316 of elongated configuration allows the teeth 312 of the pinion 278 to slide over the upper teeth or ridges 326 while providing frictional engagement to catch the pinion 278 and prevent reversal thereof.

Eventually, a close position is reached, as shown in FIG. 23. In the close position of FIG. 23, the teeth 312 of the pinion 278 engage teeth 328 at an end portion of the slot 298, so that further movement of the rack 286 to the left is not possible. This position, as shown in FIG. 23, represents an extreme opposite position in which the plunger 256 is in the close position, and the lead lock seals 270 and 272 are compressed onto the outer surfaces of the leads 300 and 302.

In accordance with the embodiment of FIGS. 19–24, however, the pinion 278 need not be rotated to the extreme close position shown in FIG. 23. Instead, the rack 286 is moved to the left, from the open position shown in FIG. 22, until it is determined that a desired amount of force is exerted on the leads 300 and 302 by the lead lock seals 270 and 272. When the force reaches the desired value, the torque wrench used to rotate the pinion 278 begins to slip, so as to torque-limit. This allows the pinion 278 to stop at the most recently past stopping location within the toothed slot 298. A plurality of such locations are defined by engagement of the teeth 312 of the pinion 278 with different combinations of the larger teeth 314 of the lower portion 318 and the smaller teeth or ridges 326 of the upper portion 316. When the torque wrench torque-limits and is removed, the smaller teeth or ridges 316 at the upper portion of the slot 298 provide sufficient frictional engagement of the teeth 312 of the pinion 278 so as to hold the pinion 278 in this position and prevent reversal in response to the resilient urging of the lead lock seals 270 and 272.

The manner in which the teeth 312 of the pinion 278 engage the small teeth or ridges 326 provides a large number of incremental positions of the rack 286, and consequently a high degree of resolution. A position is defined when an adjacent pair of the pinion teeth 312 span a trough between the small teeth or ridges 326 as well as when one of the pinion teeth 312 resides in the trough. Consequently, in one mechanism actually constructed, a stop position was defined at each 0.0035 inch of rack movement.

In this manner, the rack and pinion actuator mechanism 252 provides stepped displacement and stepped force, so that a desired amount of force is exerted on the leads independent of the hardness and the diameter of the leads. At the same time, an advantageous side actuated design is provided. The large number of stopping locations of the pinion 278 along the length of the slot 298 provides the rack and pinion actuator mechanism 252 with a substantial amount of displacement and force resolution.

As previously noted, the connector assembly 20 of FIGS. 2–9 has a fixed displacement, so that the force on the leads varies with the hardness and the diameter of the leads. Consequently, the system compliance is defined by the cold flow of the lead lock seals, which are typically made of materials such as ETR silicone, and the deflection (principally bending deflection) of the individual parts. The parts of the mechanism are commonly made from plastics, such as polysulphone, and metals, such as titanium. During actuation, the loads developed in the parts increase, causing the parts to bend or deflect.

In an actual embodiment of the connector assembly 20 of FIGS. 2–9, the cam actuator 36 rotates approximately 180° between the open and close positions, providing approximately 0.030 inches of travel of the cam slide 72. Because the plunger 32 is coupled to the cam slide 72, it moves the same distance. The lead lock seals 82 and 84 are captured within the annular recesses 86 and 88 at the front end 30 of the molded support 22. As the plunger 32 moves toward the molded support 22, in response to rotation of the cam actuator 36, the seals 82 and 84 are compressed and deformed. Because the seals can only distort in an inward direction, the cavity therein is reduced. With leads present, the necking down of the seals causes the seals 82 and 84 to compress onto the outer diameters of the leads, thereby fixing the leads in place and sealing against external fluids.

Figure 25:
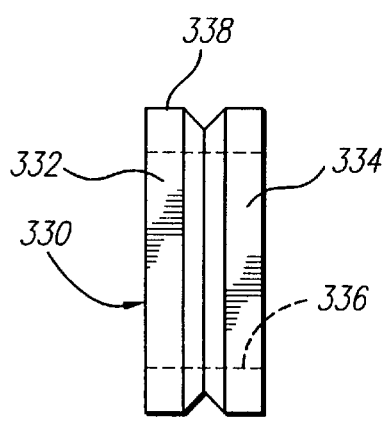
FIG. 25 is a side view of a lead lock seal, in an uncompressed state.
Figure 26:
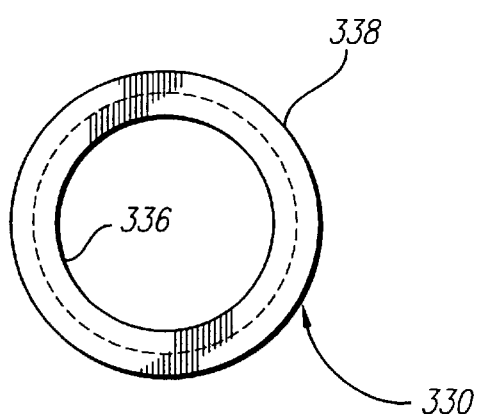
FIG. 26 is a front view of the uncompressed lead lock seal of FIG. 25.

The manner in which lead lock seals, such as the seals 82 and 84 of the embodiment of FIGS. 2–9, deform is shown in FIGS. 25–28. FIGS. 25 and 26 are respectively side and front views of a lead lock seal 330 which is in an uncompressed state. As shown in FIG. 25, the seal 330 is comprised of opposite halves 332 and 334 which together define an inner diameter 336 of the seal 330. The inner diameter 336 is represented by dotted lines in FIG. 25 and by a solid line in FIG. 26. The opposite halves 332 and 334 also define an outer diameter 338 of the seal 330.

Figure 27:
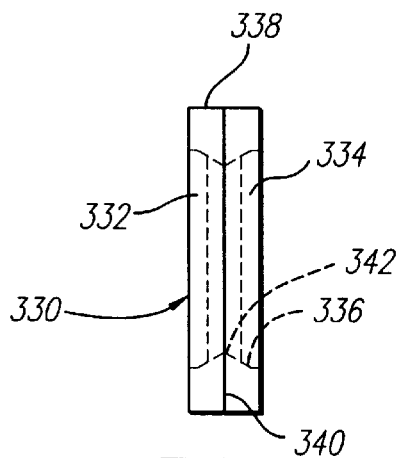
FIG. 27 is a side view of the lead lock seal of FIG. 25 showing the shape it assumes when compressed onto a lead.
Figure 28:
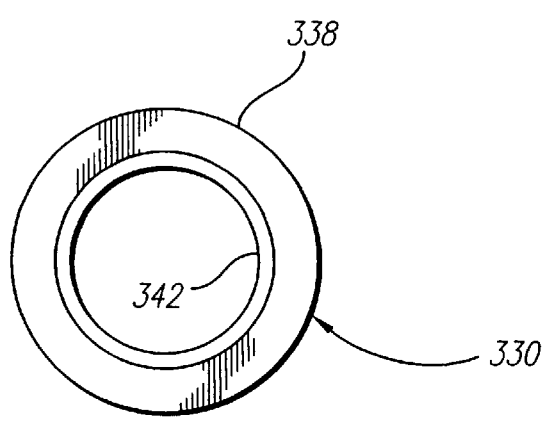
FIG. 28 is a front view of the compressed lead lock seal of FIG. 27.

FIGS. 27 and 28 are respectively side and front views of the lead lock seal 330 as compressed by movement of the plunger 32 into the close position. As shown in FIG. 27, the opposite halves 332 and 334 are pushed together, in an axial direction, so as to be joined at a common diameter 340. The outer diameter 338 is flattened, as shown in FIG. 27. However, the inner diameter 336 becomes curved in cross-sectional shape, as illustrated by dotted lines in FIG. 27. A central portion of the inner diameter 336 defines a portion 342 of minimum diameter, as shown by the dotted lines in FIG. 27 and by a solid line in FIG. 28. As shown in FIG. 28, the portion 342 of minimum diameter, with the seal 330 in the compressed state, is considerably smaller than the inner diameter 336 with the seal 330 in the uncompressed state, as shown in FIG. 26. It is this action which causes the seal 330 to neck down onto the outer surface of the lead, as the seal is compressed.

Current specifications allow the diameters of the leads to vary, to some extent. Consequently, in the case of leads of smaller diameter, the plunger must move a greater distance to exert the same force on the outer surface of the leads, as compared with leads of larger diameter. For example, the plunger may move 0.025 inches to develop a specific force on a lead of smaller diameter. At the same time, the plunger may only have to move 0.015 inch to develop the same force on a lead of larger diameter. In a fixed displacement design, such as the connector assembly 20 of FIGS. 2–9, the additional 0.010 inch displacement of the plunger (from 0.015 inch displacement to 0.025 inch displacement) can result in the development of additional forces in the mechanism. Since the developed force due to displacement is non-linear, the extra 0.010 inch of travel can result in extraordinarily high forces on leads of larger diameter. The mechanism can fail if the forces become too great.

When designing a cam actuator mechanism, if 0.025 inch of displacement is needed in order to retain a lead of smaller diameter, then the fixed displacement of the cam actuator is typically chosen at a greater value such as 0.030 inch. Consequently, the cam slider undergoes 0.030 inch of displacement before reaching the lock position. This additional displacement to reach the lock position compounds the high force problem in the case of leads of larger diameter. Consequently, the provision of additional compliance for the mechanism would be a desirable feature. Such additional compliance is provided by a fourth embodiment of a connector assembly 350, which is shown and described in connection with FIGS. 29–33.

Figure 29:
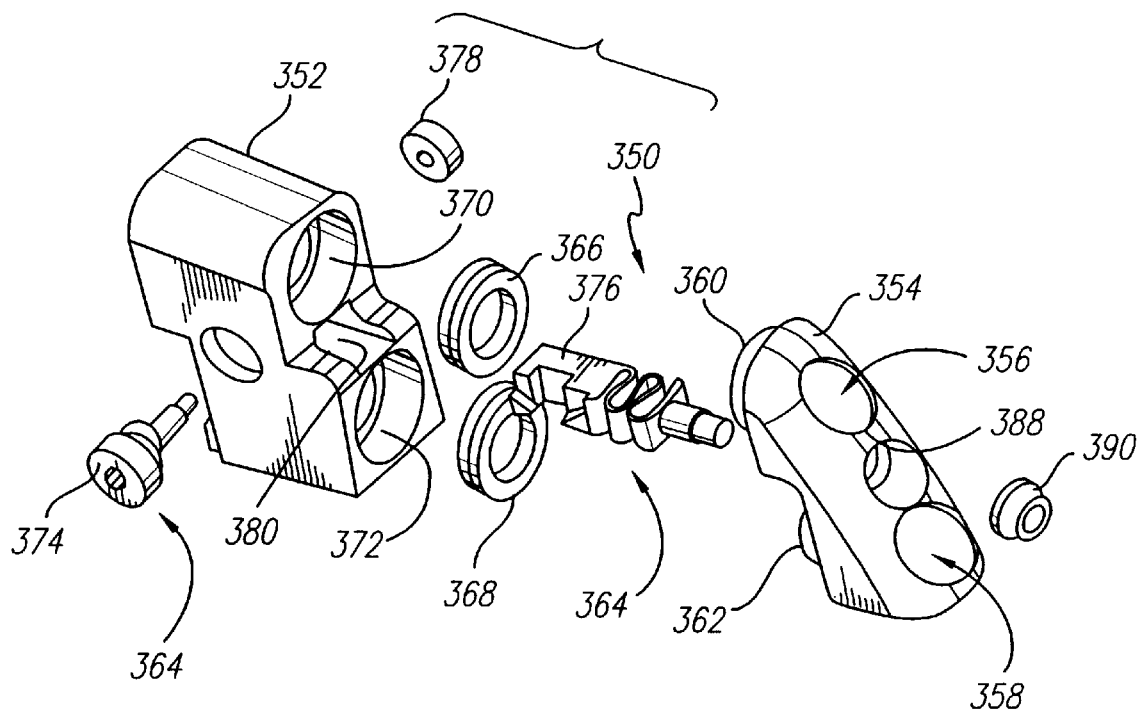
FIG. 29 is an exploded perspective view of a fourth embodiment of a connector assembly in accordance with the invention.

FIG. 29 is an exploded perspective view of the connector assembly 350 of the fourth embodiment. The various parts of the connector assembly 350 are similar to those of the connector assembly 20 of FIGS. 2–9. The principal differences lie in the details of the actuator mechanism, and particularly in configuring a portion of the cam slider as a spring. This is shown in FIG. 29, and in considerably greater detail in FIG. 30.

As in the case of the connector assembly 20 of FIGS. 2–9, the connector assembly 350 of FIG. 29 includes a molded support 352 and a plunger 354. The plunger 354 has a pair of chambers forming lead receptacles 356 and 358, which terminate at the opposite side of the plunger 354 in annular lip portions 360 and 362. Movement of the plunger 354 towards the molded support 352 by a cam actuator mechanism 364 compresses a pair of lead lock seals 366 and 368 within annular recesses 370 and 372 in the molded support 352.

The cam actuator mechanism 364 includes a cam actuator 374 and a cam slide 376. The cam actuator 374 is configured like and operates in the same manner as the cam actuator 36 of the connector assembly 20 of FIGS. 2–9. A cam retainer 378 coupled to the opposite end of the cam actuator 374 maintains the cam actuator 374 rotably journaled within the molded support 352. The cam slide 376, which is mounted for sliding movement within a slot 380 in the molded support 352, is engaged by the cam actuator 374 in the same manner that the cam slide 72 is engaged by the cam actuator 36 in the connector assembly 20 of FIGS. 2–9. However, the cam slide 376 is different from the cam slide 72 of the connector assembly 20 of FIGS. 2–9 in several respects, as shown in FIG. 29 and particularly in the detailed showing of FIG. 30. For one thing, the cam slide 376 has a portion thereof formed into a spring 382. The spring 382 extends between the main portion of the cam slide 376 and a front end 384, where the cam slide 376 is coupled to the plunger 354. The front end 384 has a threaded portion 386 which extends through an aperture 388 in the plunger 354 and receives a threaded nut 390 thereon. The aperture 388 is located between the lead receptacles 356 and 358.

The spring 382 of the cam slide 376 provides the cam actuator mechanism 364 with considerable compliance. This prevents excessive force from being exerted on leads of larger diameter, in the fixed displacement configuration of the connector assembly 350. If the cam actuator 374 is rotated so as to produce a displacement of 0.030 inch of the cam slide 376, the plunger 354 is moved somewhat less due to the compliance of the spring 382. The additional compliance provided by the spring 382 helps to maintain a more linear relationship of force with deflection, compared with the basically non-compliant configuration of the connector assembly 20 of FIGS. 2–9, as illustrated in FIG. 31 described hereafter.

Figure 31:
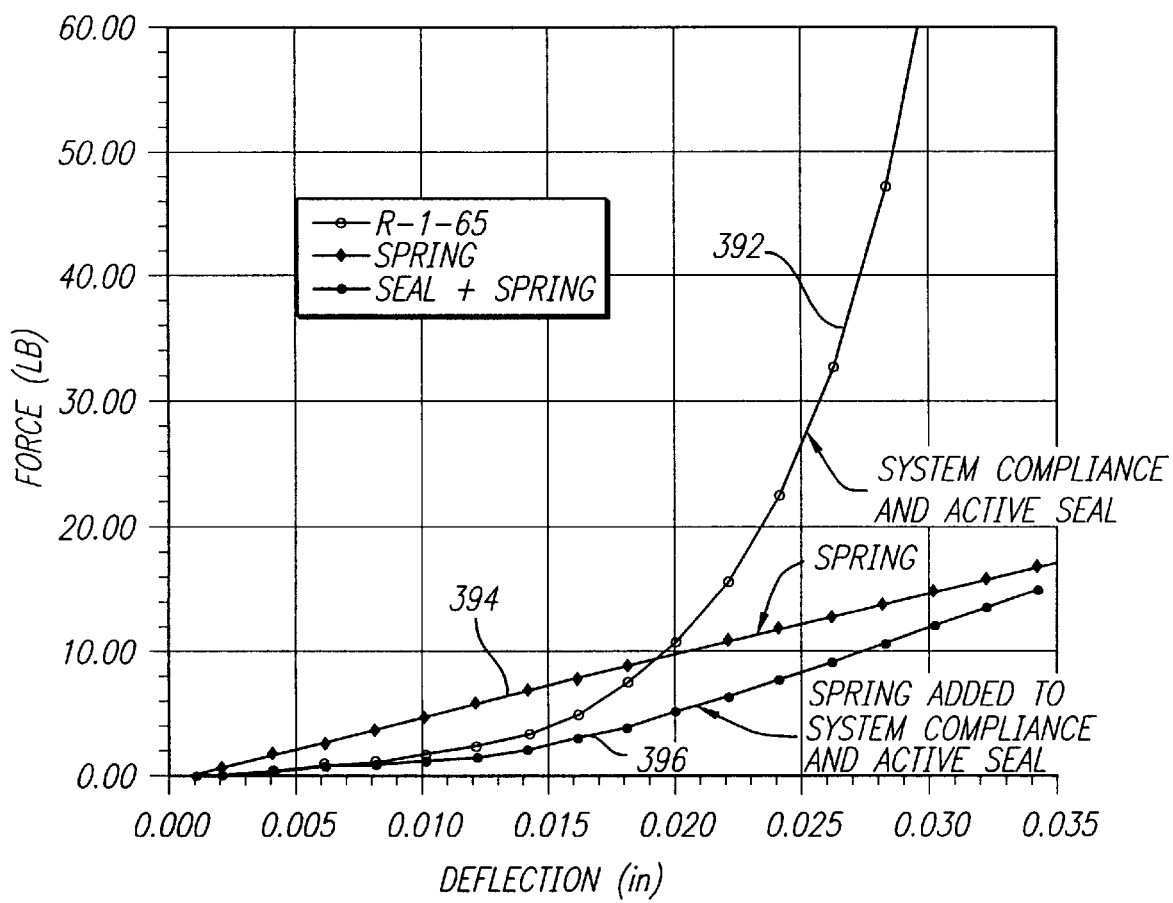
FIG. 31 is a diagrammatic plot of force as a function of deflection, for the connector assembly of FIG. 30.

FIG. 31 is a diagramatic plot of force as a function of deflection. A first plot 392 represents force versus deflection for a connector assembly such as the assembly 20 of FIGS. 2–9 in which the cam slide has no spring. Consequently, the only compliance present is that due to the compliance of the parts of the mechanism. As deflection increases, the force exerted on the lead increases at a greater and greater rate. Thus, up to a deflection of approximately 0.020 inch, the force increases gradually from 0 to a value just over 10.00 lbs. However, as the deflection then continues to increase from 0.020 inch to 0.025 inch, the force increases to almost 30.00 lbs. Continued displacement produces forces which increase at even greater rates.

Figure 30:
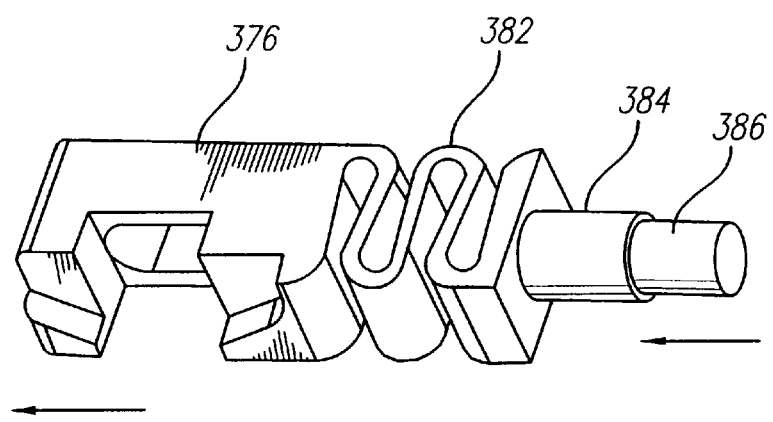
FIG. 30 is a perspective view of the cam slide of the connector assembly of FIG. 29.

A second plot 394 of FIG. 31 represents force as a function of deflection, for just the spring 382 of the cam slider 376 of FIGS. 29 and 30. As shown, the spring 382 provides an essentially linear relationship between force and deflection. As the deflection increases, the force increases in essentially linear fashion.

If the compliance provided by the spring 382 is combined with the plot 392, which represents the connector assembly 20 in FIGS. 2–9 without the included spring, then the result is a plot 396 shown in FIG. 31. It will be seen that the combined plot 396 is almost linear in nature, particularly when contrasted with the plot 392. As the deflection increases, the force also increases. The rate of force increase is slightly greater with increasing deflection, but is nowhere close to the greatly accelerated force increase represented by the plot 392. Consequently, it will be appreciated that the presence of the spring 382 in the cam slide 376 provides an almost linear relationship between force and deflection, thereby preventing excessive force from being applied to the leads and particularly those of larger diameter.

Figure 32:
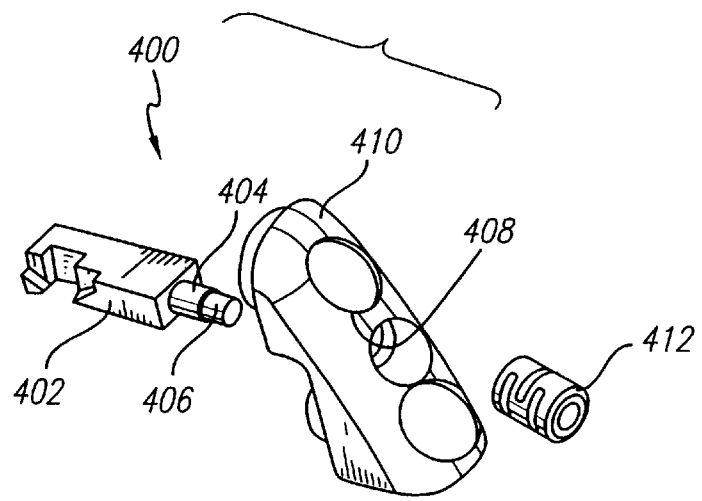
FIG. 32 is an exploded perspective view of a variation of the fourth embodiment of FIG. 29, which uses a compliant nut.
Figure 33:
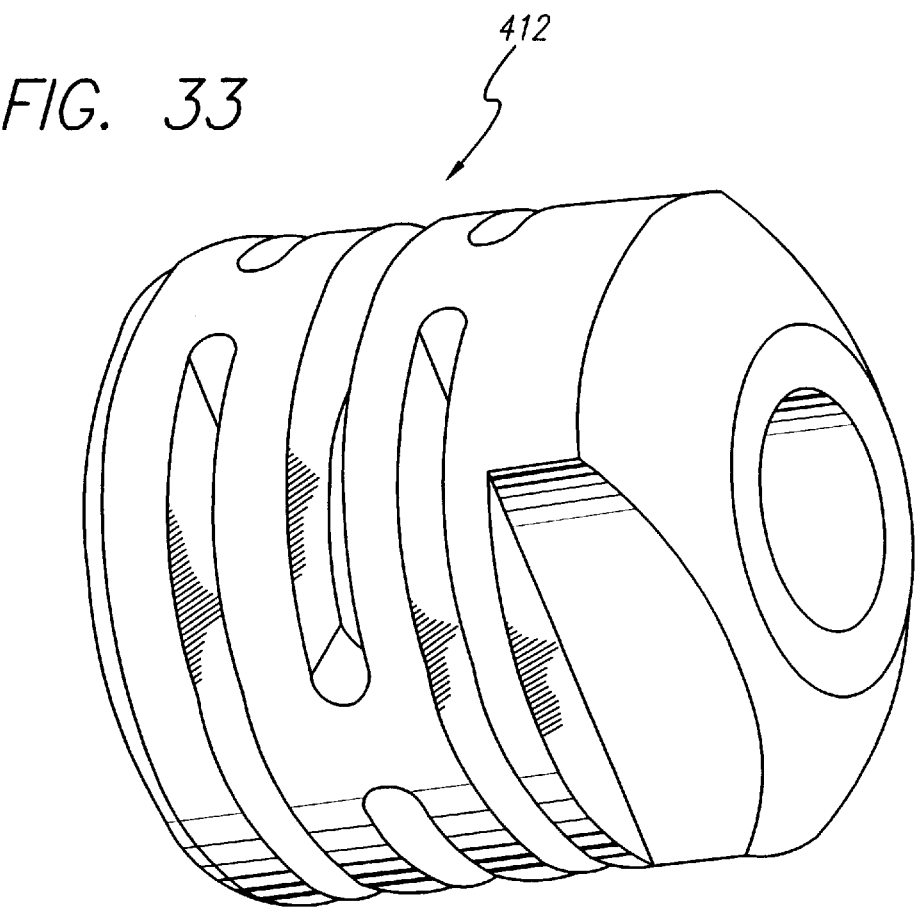
FIG. 33 is an enlarged perspective view of the compliant nut of FIG. 32.

FIG. 32 is an exploded perspective view of a portion of a connector assembly 400 which is an alternative embodiment of the connector assembly 350 of FIGS. 29–31. The connector assembly 400 includes a cam slide 402. Like the cam slide 376 of the connector assembly 350 of FIGS. 29–31, the cam slide 402 of the connector assembly 400 has a forward end 404 which terminates in a threaded portion 406. The threaded portion 406 extends through an aperture 408 in a plunger 410 of the connector assembly 400. However, unlike the cam slider 376, the cam slider 402 has no spring. Instead, the threaded portion 406 of the forward end 404 receives a compliant or "spring" nut 412 on the opposite of the plunger 410 from the major portion of the cam slider 402. The compliant nut 412, which provides compliance much in the same manner as the spring 382 of the cam slider 376, is shown in enlarged and detailed fashion in FIG. 33. As shown therein, the compliant nut 412 behaves much like a spring when mounted on the threaded portion 406 of the cam slider 402. The resulting compliance enables the connector assembly 400 of FIG. 32 to prevent excessive force from being exerted, particularly on leads of large diameter, much in the same manner as the connector assembly 350 shown in FIGS. 29–31.

While the invention has been described in connection with preferred embodiments, it will be understood that it is not intended to limit the invention thereto, but that it is intended to cover all modifications and alternative constructions falling within the spirit and scope of the invention as expressed in the appended claims.

What is claimed is:

1. A connector assembly for an implantable medical device comprising:

a support having a pair of apertures therein;

a pair of connector bore assemblies coupled to and extending from the apertures in the support and adapted to make electrical contact with leads inserted therein;

a plunger movably coupled to the support and having a pair of apertures therein aligned with the apertures in the support, the pair of apertures in the support and the pair of apertures in the plunger combining with the pair of connector bore assemblies to define a pair of lead-receiving bores;

a pair of locking seals disposed within the lead-receiving bores; and means for selectively moving the plunger relative to the support to compress the locking seals and thereby fix and form seals around leads disposed in the lead-receiving bores.

2. The connector assembly, as defined in claim 1, wherein the support is made of molded material, and further including a mass of epoxy extending from the support and encapsulating the pair of connector bore assemblies therein.

3. The connector assembly, as defined in claim 1, wherein each of the pair of apertures in the support has an annular recess therein adjacent the plunger for receiving one of the pair of locking seals therein, and the locking seals comprise ring-shaped seals of elastomeric material.

4. The connector assembly, as defined in claim 2, further including a fastener assembly on the support for mounting the support on an implantable medical device.

5. In an implantable medical device having electronic circuits within a sealed housing, a connector assembly disposed at the outside of the housing for receiving a first and second lead and for electrically coupling the first and second lead to the electronic circuits within the sealed housing, the connector assembly comprising:

a main body having a first and second receptacle adapted to receive the first and second leads;

sealing means, made of compressable material and disposed within the first and second receptacles, for providing a seal around each of the first and second leads;

compressing means for compressing the sealing means around the first and second leads, thereby forming a first and a second fluid-tight seal, respectively; and actuating means, coupled to the compressing means, for selectively locking and unlocking the first and second leads in place.

6. The connector assembly, as defined in claim 5, wherein the compressing means comprises:

a plunger, coupled to the main body, having bi-directional movement along a central axis of the lead; and wherein the plunger simultaneously compresses both the first and the second leads within the first and second receptacles, respectively.

7. The connector assembly, as defined in claim 6, wherein: the plunger has a shape that mates with the main body and further forms a portion of the connector assembly.

8. The connector assembly, as defined in claim 6, wherein the actuating means is responsive to a torquing force.

9. The connector assembly, as defined in claim 8, wherein: the main body comprises a slide aperture; and the actuator means comprises a cam slide, located within the slide aperture, and a cam actuator rotatably coupled to the cam slide, the cam actuator translating a rotational force to a longitudinal force along the central axis onto the plunger to thereby force the plunger against the main body.

10. The connector assembly, as defined in claim 8, wherein:

the main body has a slide aperture generally parallel to the central axis and a cam aperture generally perpendicular to and intersecting the slide aperture;

the actuating means comprises an elongated cam slide, coupled to the plunger and slidably disposed within the slide aperture, and a cam actuator rotatably disposed within the cam aperture;

wherein the cam actuator is rotatable between a locking position, in which the sealing means engages and seals the lead, and an unlocking position, in which the sealing means is disengaged from the lead to permit removal of the lead from the lead receptacle.

11. The connector assembly, as defined in claim 8, wherein:

the main body comprises a rack aperture;

the actuator means comprises a rack located within the rack aperture and slidably coupled to the plunger, the rack further having a toothed slot therein, and a toothed pinion rotatably coupled within the toothed slot.

12. The connector assembly, as defined in claim 8, wherein:

the plunger includes a threaded recess adjacent the first and second lead receptacles; and the actuating means comprises a threaded screw received within the threaded recess which provides a longitudinal force along the central axis onto the plunger to thereby force the plunger against the main body.

13. The connector assembly, as defined in claim 8, wherein:

the main body comprises a rack aperture generally parallel to the central axis, and a pinion aperture extending generally perpendicular to and intersecting the rack aperture; and the actuator means comprising an elongated rack coupled to the plunger and slidably disposed within the rack aperture and having a toothed slot therein extending through the rack in a direction generally perpendicular to the central axis, and a toothed pinion rotatably disposed within the pinion aperture, the toothed pinion extending through the toothed slot in the rack.

14. The connector assembly, as defined in claim 13, wherein:

the toothed slot has a plurality of relatively large teeth on a bottom portion thereof and a plurality of relatively small teeth on a top portion thereof; and the pinion has a plurality of teeth around a circumference thereof which mesh with the relatively large teeth on the bottom portion of the toothed slot and engage the relatively small teeth on the top portion of the toothed slot to define a plurality of stepped positions of the pinion as it rotates within the toothed slot.

15. The connector assembly, as defined in claim 13, wherein the toothed slot has a first end thereof defining a fully closed stopping position.

16. The connector assembly, as defined in claim 15, wherein the toothed slot has a second end thereof opposite the first end which defines a fully opened position, the second end being configured to allow the pinion to free spin with further rotation thereof when the pinion reaches the second end.

17. The connector assembly, as defined in claim 16, wherein the toothed slot has at least one intermediate stopping location along the rack which provides a stepped-force, so that a desired amount of force is exerted on the first and second leads.

18. The connector assembly, as defined in claim 16, wherein the toothed slot has a plurality of intermediate stopping locations along the rack, the plurality of intermediate stopping locations providing a higher resolution stepped-displacement and stepped-force, so that a desired amount of force is exerted on the first and second leads.

19. The connector assembly, as defined in claim 18, wherein:

the main body includes an annular recess; and the sealing means comprises an annular seal made of elastomeric material, the annular seal being located within the annular recess.

20. The connector assembly, as defined in claim 19, wherein:

the compressing means includes a plunger axially movable relative to the annular recess and having an annular portion for engaging the annular seal; and the actuation means includes a mechanism for moving the plunger to selected axial positions relative to the annular recess.

21. The connector assembly, as defined in claim 20, wherein the mechanism for moving the plunger is movable between a first position in which the seal engages the lead to fix the lead in place and form a seal there around and a second position in which the seal is disengaged from the lead to permit removal of the lead from the lead receptacle.

22. The connector assembly, as defined in claim 20, wherein the slide is mounted in the main body for sliding movement in a direction of elongation of the lead receptacle and has an aperture therein for receiving the offset cam.

23. The connector assembly, as defined in claim 22, wherein the slide has a resilient portion thereof for providing the mechanism with increased compliance.

24. In an implantable medical device having electronic circuits within a sealed housing, a connector assembly disposed at the outside of the housing for receiving a lead and for electrically coupling the lead to the electronic circuits within the sealed housing, the connector assembly comprising:
- a main body having a receptacle adapted to receive the lead;
- sealing means, made of compressable material and disposed within the receptacle, for sealing around the lead;
- compressing means, dimensioned to mate with the main body, for compressing the sealing means around the lead; and
- actuation means for selectively locking and unlocking the lead in place, the actuation means including a slide coupled to the compressing means and an offset cam rotatably coupled to the slide, wherein the offset cam causes the slide to exert a force between the compressing means and the main body so that the sealing means is compressed against the lead to form a fluid-tight seal.

25. The connector assembly, as defined in claim 24, wherein the screw extends in a direction of elongation of the receptacle, and is rotatably journaled within the compressing means and has a tool receiving receptacle mounted thereon.

26. In an implantable medical device having electronic circuits within a sealed housing, a connector assembly disposed at the outside of the housing for receiving a lead and for electrically coupling the lead to the electronic circuits within the sealed housing, the connector assembly comprising:
- a main body having a receptacle, adapted to receive the lead, and a threaded recess adjacent the receptacle;
- sealing means, made of compressable material and disposed within the receptacle, for sealing around the lead;
- compressing means, dimensioned to mate with the main body, for compressing the sealing means around the lead; and
- actuating means for selectively locking and unlocking the lead in place, the actuating means including a screw for engagement within the threaded recess and advancable and retractable therein, wherein the screw, when advanced, exerts a force between the compression means and the main body so that the sealing means is compressed against the lead to form a fluid-tight seal.

27. In an implantable medical device having electronic circuits within a sealed housing, a connector assembly disposed at the outside of the housing for receiving a lead and for electrically coupling the lead to the electronic circuits within the sealed housing, the connector assembly comprising:
- a main body having a receptacle adapted to receive the lead;
- sealing means, made of compressable material and disposed within the receptacle, for sealing around the lead;
- compressing means, dimensioned to mate with the main body, for compressing the sealing means around the lead; and
- actuating means for selectively locking and unlocking the lead in place, the actuating means including a rack and pinion assembly, coupled to the compression means, which exerts a force between the compression means and the main body so that the sealing means is compressed against the lead to form a fluid-tight seal.

28. The connector assembly, as defined in claim 27, wherein:
- the compressing means comprises a plunger axially movable towards the main body, the plunger having an annular portion for engaging the sealing means;
- the rack is disposed within a slide which is directly coupled to the plunger, wherein the pinion, when coupled to the rack, causes the slide to move towards the main body, thereby causing the annular portion of the plunger to compress the sealing means to the form a fluid-tight seal.

29. The connector assembly, as defined in claim 28, wherein:
- the rack comprises a plurality of toothed slots which define a plurality of stepped positions for the pinion, wherein the pinion rotates within the plurality of toothed slots causes the slide to exert a step-wise increase in force between the plunger and the main body so that the sealing means is compressed to form a fluid-tight seal.

30. In an implantable medical device having electronic circuits within a sealed housing, a connector assembly disposed at the outside of the housing for receiving a lead and for electrically coupling the lead to the electronic circuits within the sealed housing, the connector assembly comprising:
- a main body having a receptacle adapted to receive the lead;
- sealing means, made of compressable material and disposed within the receptacle, for sealing around the lead;
- compressing means, dimensioned to mate with the main body, for compressing the sealing means around the lead; and
- actuating means, coupled to the compressing means, for selectively locking and unlocking the lead in place using a variable amount of displacement to accommodate a desired lead having a desired lead diameter;
- whereby a substantially uniform force is exerted on the sealing means independent of lead diameter.

31. The connector assembly, as defined in claim 30, wherein:
- the main body comprises a threaded recess adjacent the receptacle; and
- the actuating means comprises a screw for engagement within the threaded recess and advancable and retractable therein, wherein the screw, when advanced by a torque wrench, exerts a force between the compression means and the main body so that the sealing means is compressed against the lead to form a fluid-tight seal, wherein the screw will be limited when a desired amount of force is delivered to the desired lead.

32. The connector assembly, as defined in claim 30, wherein:

the actuating means comprises a rack and pinion assembly, the rack being disposed within a slide which is coupled to the compression means, the rack having a plurality of toothed slots which define a plurality of stepped positions for the pinion, wherein the pinion, when coupled to the rack, rotates within the plurality of toothed slots causes the slide to exert a step-wise increase in force between the compression means and the main body so that the sealing means is compressed against the lead to form a fluid-tight seal; wherein the pinion, when advanced by a torque wrench, will be limited when a desired amount of force is delivered to the desired lead.

33. The connector assembly, as defined in claim 30, wherein:

the actuating means comprises a slide coupled to the compressing means and an offset cam rotatably coupled to the slide, the slide further have a spring formed therein, wherein rotation of the offset cam causes a linear displacement on the slide, which displacement is varied by the spring to produce a substantially linear force between the compressing means and the main body, so that the sealing means is compressed against the lead to form a fluid-tight seal.

34. The connector assembly, as defined in claim 30, wherein:

the actuating means comprises a slide coupled to the compressing means and an offset cam rotatably coupled to the slide, the slide being coupled to a spring nut, wherein rotation of the offset cam causes a linear displacement on the slide, which displacement is varied by the spring nut to produce a substantially linear force between the compressing means and the main body, so that the sealing means is compressed against the lead to form a fluid-tight seal.

35. The connector assembly, as defined in claim 34, wherein the cam slide has a spring formed therein, the spring having a predetermined amount of compliance so that a constant displacement exerted on the slide produces a substantially linear force between the main body and the plunger.

36. The connector assembly, as defined in claim 34, wherein the cam slide is coupled to the plunger by a spring nut, the spring nut having a predetermined amount of compliance so that a constant displacement exerted on the slide produces a substantially linear force between the main body and the plunger.

37. The connector assembly, as defined in claim 34, wherein:

the cam slide has a cam aperture for receiving the cam actuator and a pair of limit surfaces on opposite sides of the cam aperture; and the cam actuator has a lobe extending therefrom which engages the pair of limit surfaces to define lock and unlock positions.

38. The connector assembly, as defined in claim 34, wherein the cam actuator has an enlarged head at an end thereof disposed outside of a first side of the support and having a drive-tool-receiving recess therein, and further including an enlarged cam retainer mounted on an end of the cam actuator opposite the enlarged head and disposed outside of an opposite second side of the support.

39. The connector assembly, as defined in claim 38, wherein the drive-tool-receiving recess of the enlarged head is adapted to receive a torque wrench for rotatably driving the cam actuator.

40. A connector assembly for releasably fixing and sealing a lead for an implantable medical device, comprising:

a support having a receptacle and a bore assembly for receiving the lead, the bore assembly having at least one contact therein for making electrical contact with the lead when a lead is seated therein;

an annular seal of deformable material seated in the receptacle;

a plunger, coupled to the support, having means for compressing the annular seal, the plunger chamber combining with the support chamber and the bore assembly to form the lead receptacle; and a cam slide, coupled to the plunger, and a cam actuator rotatably coupled to the cam slide, the cam actuator translating a rotational force to a longitudinal force onto the plunger to thereby force the plunger against the main body which selectively compresses the annular seal against the outside of a lead to thereby fix in place and seal around the lead.

41. The connector assembly, as defined in claim 40, wherein the screw has an enlarged keeper at the first end thereof, and further including a retainer clip disposed within the first aperture between the screw block and the keeper and having an aperture therein which receives a portion of the screw therein and which is smaller than the keeper.

42. The connector assembly, as defined in claim 40, wherein the enlarged driver has a drive-tool-receiving recess therein.

43. The connector assembly, as defined in claim 42, wherein the drive-tool-receiving recess of the enlarged driver is adapted to receive a torque wrench for rotatably driving the screw.

44. A connector assembly for releasably fixing and sealing a lead for an implantable medical device, comprising:

a support having a receptacle and a bore assembly for receiving the lead, the bore assembly having at least one contact therein for making electrical contact with the lead when a lead is seated therein, the support having a threaded screw block within a first aperture;

an annular seal of deformable material seated in the receptacle;

a plunger, coupled to the support, having means for compressing the annular seal, the plunger chamber combining with the support chamber and the bore assembly to form the lead receptacle, the plunger having a second aperture aligned with the first aperture of the support; and a screw, rotatably disposed within the first and second apertures, having a threaded portion at a first end for connection with the screw block and an enlarged driver at a second end, wherein the enlarged driver, when rotated, selectively compresses the annular seal against the outside of a lead to thereby fix in place and seal around the lead.

45. The connector assembly, as defined in claim 44, wherein:

the toothed slot has a plurality of relatively large teeth on a bottom portion thereof and a plurality of relatively small teeth on a top portion thereof; and the pinion has a plurality of teeth around a circumference thereof which mesh with the relatively large teeth on the bottom portion of the toothed slot and engage the relatively small teeth on the top portion of the toothed slot to define a plurality of stepped positions of the pinion as it rotates within the toothed slot.

46. The connector assembly, as defined in claim 45, wherein the toothed slot has a second end thereof opposite the first end which defines a closed position.

47. The connector assembly, as defined in claim 45, wherein the toothed slot has a first end thereof defining an open position configured to allow the pinion to free spin with further rotation thereof when the pinion reaches the first end.

48. The connector assembly, as defined in claim 47, wherein the rack has a thin, elongated upper portion thereof defining an upper portion of the toothed slot, the upper portion being separated from and being resiliently movable relative to an opposite lower portion of the rack defining a lower portion of the toothed slot.

49. The connector assembly, as defined in claim 48, wherein the upper and lower portions have nubs which engage walls of the rack aperture to limit separation of the upper portion from the lower portion when the pinion is moved from the end of the toothed slot.

50. A connector assembly for releasably fixing and sealing a lead for an implantable medical device, comprising:

- a support having a receptical and a bore assembly for receiving the lead, the bore assembly having at least one contact therein for making electrical contact with the lead when a lead is seated therein;
- an annular seal of deformable material seated in the receptical;
- a plunger, coupled to the support, having means for compressing the annular seal, the plunger chamber combining with the support chamber and the bore assembly to form the lead receptacle;
- an elongated slide, coupled to the plunger and slidably disposed within the support, having a rack with a toothed slot therein; and
- a pinion, rotatably disposed within the toothed slot, wherein the pinion, when rotated, selectively compresses the annular seal against the outside of a lead to thereby fix in place and seal around the lead.

* * * * *